US00RE42753E

(19) United States
(12) Reissued Patent
Kiani-Azarbayjany et al.

(10) Patent Number: US RE42,753 E
(45) Date of Reissued Patent: Sep. 27, 2011

(54) ACTIVE PULSE BLOOD CONSTITUENT MONITORING

(75) Inventors: Esmaiel Kiani-Azarbayjany, Laguna Niguel, CA (US); Mohamed Kheir Diab, Ladera Ranch, CA (US); James M. Lepper, Jr., Whittier, CA (US)

(73) Assignee: MASIMO Laboratories, Inc., Irvine, CA (US)

(21) Appl. No.: 12/497,517

(22) Filed: Jul. 2, 2009

Related U.S. Patent Documents

Reissue of:
(64) Patent No.: 7,239,905
Issued: Jul. 3, 2007
Appl. No.: 11/204,585
Filed: Aug. 16, 2005

U.S. Applications:
(63) Continuation of application No. 09/706,965, filed on Nov. 6, 2000, now Pat. No. 6,931,268, which is a continuation of application No. 09/190,719, filed on Nov. 12, 1998, now Pat. No. 6,151,516, which is a continuation of application No. 08/843,863, filed on Apr. 17, 1997, now Pat. No. 5,860,919, which is a continuation of application No. 08/482,071, filed on Jun. 7, 1995, now Pat. No. 5,638,816.

(51) Int. Cl.
*A61B 5/00* (2006.01)
*A61B 5/1455* (2006.01)

(52) U.S. Cl. ..... 600/316; 600/322

(58) Field of Classification Search ..... 600/310, 600/316, 322, 323
See application file for complete search history.

(56) References Cited

U.S. PATENT DOCUMENTS 3,482,565 A 12/1969 Gowen
3,704,708 A 12/1972 Iberall
3,771,857 A 11/1973 Thomasson et al.
(Continued)

FOREIGN PATENT DOCUMENTS

JP 03126104 A2 5/1991
(Continued)

OTHER PUBLICATIONS

Fine, I. et al. "RBC Aggregation assisted light transmission through blood and Occlusion Oximetry," 10 pages.

(Continued)

*Primary Examiner* — Eric Winakur
(74) *Attorney, Agent, or Firm* — Knobbe Martens Olson & Bear LLP

(57) ABSTRACT

A blood constituent monitoring method for inducing an active pulse in the blood volume of a patient. The induction of an active pulse results in a cyclic, and periodic change in the flow of blood through a fleshy medium under test. By actively inducing a change of the blood volume, modulation of the volume of blood can be obtained to provide a greater signal to noise ratio. This allows for the detection of constituents in blood at concentration levels below those previously detectable in a non-invasive system. Radiation which passes through the fleshy medium is detected by a detector which generates a signal indicative of the intensity of the detected radiation. Signal processing is performed on the electrical signal to isolate those optical characteristics of the electrical signal due to the optical characteristics of the blood.

12 Claims, 16 Drawing Sheets

U.S. PATENT DOCUMENTS

| | | | | | |
|---|---|---|---|---|---|
| 3,914,464 | A | | 10/1975 | Thomasson et al. | |
| 3,981,568 | A | | 9/1976 | Bartolomei | |
| 4,406,289 | A | | 9/1983 | Wesseling et al. | |
| 4,407,290 | A | | 10/1983 | Wilber | |
| 4,883,055 | A | | 11/1989 | Merrick | |
| 4,927,264 | A | | 5/1990 | Shiga et al. | |
| 4,957,371 | A | | 9/1990 | Pellicori et al. | |
| 4,960,128 | A | | 10/1990 | Gordon et al. | |
| 4,964,408 | A | | 10/1990 | Hink et al. | |
| 5,007,423 | A | | 4/1991 | Branstetter et al. | |
| 5,041,187 | A | | 8/1991 | Hink et al. | |
| 5,069,213 | A | | 12/1991 | Polczynski | |
| 5,077,476 | A | | 12/1991 | Rosenthal | |
| 5,111,817 | A | | 5/1992 | Clark et al. | |
| 5,163,438 | A | | 11/1992 | Gordon et al. | |
| 5,183,042 | A | | 2/1993 | Harjunmaa et al. | |
| 5,200,855 | A | | 4/1993 | Meredith, Jr. et al. | |
| 5,282,467 | A | * | 2/1994 | Piantadosi et al. | 600/335 |
| 5,337,744 | A | | 8/1994 | Branigan | |
| 5,348,003 | A | * | 9/1994 | Caro | 600/322 |
| 5,361,758 | A | * | 11/1994 | Hall et al. | 600/322 |
| D353,195 | S | | 12/1994 | Savage et al. | |
| D353,196 | S | | 12/1994 | Savage et al. | |
| 5,372,135 | A | | 12/1994 | Mendelson et al. | |
| 5,372,136 | A | | 12/1994 | Steuer et al. | |
| 5,379,774 | A | | 1/1995 | Nishimura et al. | |
| 5,398,681 | A | | 3/1995 | Kupershmidt | |
| 5,413,100 | A | * | 5/1995 | Barthelemy et al. | 600/328 |
| 5,416,325 | A | | 5/1995 | Buontempo et al. | |
| 5,416,579 | A | | 5/1995 | Barshad et al. | |
| 5,431,170 | A | | 7/1995 | Mathews | |
| D361,840 | S | | 8/1995 | Savage et al. | |
| D362,063 | S | | 9/1995 | Savage et al. | |
| 5,452,717 | A | | 9/1995 | Branigan et al. | |
| D363,120 | S | | 10/1995 | Savage et al. | |
| 5,482,036 | A | | 1/1996 | Diab et al. | |
| 5,490,505 | A | | 2/1996 | Diab et al. | |
| 5,494,043 | A | | 2/1996 | O'Sullivan et al. | |
| 5,522,388 | A | | 6/1996 | Ishikawa et al. | |
| 5,529,755 | A | | 6/1996 | Higashio et al. | |
| 5,533,511 | A | | 7/1996 | Kaspari et al. | |
| 5,562,002 | A | | 10/1996 | Lalin | |
| 5,590,649 | A | | 1/1997 | Caro et al. | |
| 5,602,924 | A | | 2/1997 | Durand et al. | |
| 5,632,272 | A | | 5/1997 | Diab et al. | |
| 5,638,816 | A | | 6/1997 | Kiani-Azarbayjany et al. | |
| 5,638,818 | A | | 6/1997 | Diab et al. | |
| 5,645,440 | A | | 7/1997 | Tobler et al. | |
| 5,685,299 | A | | 11/1997 | Diab et al. | |
| D393,830 | S | | 4/1998 | Tobler et al. | |
| 5,743,262 | A | | 4/1998 | Lepper, Jr. et al. | |
| 5,758,644 | A | | 6/1998 | Diab et al. | |
| 5,760,910 | A | | 6/1998 | Lepper, Jr. et al. | |
| 5,769,785 | A | | 6/1998 | Diab et al. | |
| 5,782,757 | A | | 7/1998 | Diab et al. | |
| 5,785,659 | A | | 7/1998 | Caro et al. | |
| 5,791,347 | A | | 8/1998 | Flaherty et al. | |
| 5,810,734 | A | | 9/1998 | Caro et al. | |
| 5,823,950 | A | | 10/1998 | Diab et al. | |
| 5,830,131 | A | | 11/1998 | Caro et al. | |
| 5,833,618 | A | | 11/1998 | Caro et al. | |
| 5,860,919 | A | | 1/1999 | Kiani-Azarbayjany et al. | |
| 5,890,929 | A | | 4/1999 | Mills et al. | |
| 5,904,654 | A | | 5/1999 | Wohltmann et al. | |
| 5,919,134 | A | | 7/1999 | Diab | |
| 5,934,925 | A | | 8/1999 | Tobler et al. | |
| 5,940,182 | A | | 8/1999 | Lepper, Jr. et al. | |
| 5,995,855 | A | | 11/1999 | Kiani et al. | |
| 5,997,343 | A | | 12/1999 | Mills et al. | |
| 6,002,952 | A | | 12/1999 | Diab et al. | |
| 6,011,986 | A | | 1/2000 | Diab et al. | |
| 6,027,452 | A | | 2/2000 | Flaherty et al. | |
| 6,036,642 | A | | 3/2000 | Diab et al. | |
| 6,045,509 | A | | 4/2000 | Caro et al. | |
| 6,067,462 | A | | 5/2000 | Diab et al. | |
| 6,081,735 | A | | 6/2000 | Diab et al. | |
| 6,088,607 | A | | 7/2000 | Diab et al. | |
| 6,110,522 | A | | 8/2000 | Lepper, Jr. et al. | |
| 6,144,868 | A | | 11/2000 | Parker | |
| 6,151,516 | A | | 11/2000 | Kiani-Azarbayjany et al. | |
| 6,152,754 | A | | 11/2000 | Gerhardt et al. | |
| 6,157,850 | A | | 12/2000 | Diab et al. | |
| 6,165,005 | A | | 12/2000 | Mills et al. | |
| 6,184,521 | B1 | | 2/2001 | Coffin, IV et al. | |
| 6,191,860 | B1 | | 2/2001 | Klinger et al. | |
| 6,206,830 | B1 | | 3/2001 | Diab et al. | |
| 6,213,952 | B1 | | 4/2001 | Finarov et al. | |
| 6,229,856 | B1 | | 5/2001 | Diab et al. | |
| 6,236,872 | B1 | | 5/2001 | Diab et al. | |
| 6,256,523 | B1 | | 7/2001 | Diab et al. | |
| 6,263,222 | B1 | | 7/2001 | Diab et al. | |
| 6,278,522 | B1 | | 8/2001 | Lepper, Jr. et al. | |
| 6,280,213 | B1 | | 8/2001 | Tobler et al. | |
| 6,285,896 | B1 | | 9/2001 | Tobler et al. | |
| 6,321,100 | B1 | | 11/2001 | Parker | |
| 6,334,065 | B1 | | 12/2001 | Al-Ali et al. | |
| 6,343,224 | B1 | | 1/2002 | Parker | |
| 6,349,228 | B1 | | 2/2002 | Kiani et al. | |
| 6,360,114 | B1 | | 3/2002 | Diab et al. | |
| 6,371,921 | B1 | | 4/2002 | Caro et al. | |
| 6,377,829 | B1 | | 4/2002 | Al-Ali | |
| 6,388,240 | B2 | | 5/2002 | Schulz et al. | |
| 6,397,091 | B2 | | 5/2002 | Diab et al. | |
| 6,400,971 | B1 | | 6/2002 | Finarov et al. | |
| 6,400,972 | B1 | | 6/2002 | Fine | |
| 6,430,525 | B1 | | 8/2002 | Weber et al. | |
| 6,463,311 | B1 | | 10/2002 | Diab | |
| 6,470,199 | B1 | | 10/2002 | Kopotic et al. | |
| 6,501,975 | B2 | | 12/2002 | Diab et al. | |
| 6,515,273 | B2 | | 2/2003 | Al-Ali | |
| 6,519,487 | B1 | | 2/2003 | Parker | |
| 6,525,386 | B1 | | 2/2003 | Mills et al. | |
| 6,526,300 | B1 | | 2/2003 | Kiani et al. | |
| 6,541,756 | B2 | | 4/2003 | Schulz et al. | |
| 6,542,764 | B1 | | 4/2003 | Al-Ali et al. | |
| 6,580,086 | B1 | | 6/2003 | Schulz et al. | |
| 6,584,336 | B1 | | 6/2003 | Ali et al. | |
| 6,587,704 | B1 | | 7/2003 | Fine et al. | |
| 6,595,316 | B2 | | 7/2003 | Cybulski et al. | |
| 6,597,933 | B2 | | 7/2003 | Kiani et al. | |
| 6,606,511 | B1 | | 8/2003 | Ali et al. | |
| 6,632,181 | B2 | | 10/2003 | Flaherty et al. | |
| 6,640,116 | B2 | | 10/2003 | Diab | |
| 6,643,530 | B2 | | 11/2003 | Diab et al. | |
| 6,650,917 | B2 | | 11/2003 | Diab et al. | |
| 6,654,624 | B2 | | 11/2003 | Diab et al. | |
| 6,658,276 | B2 | | 12/2003 | Kiaul et al. | |
| 6,661,161 | B1 | | 12/2003 | Lanzo et al. | |
| 6,671,531 | B2 | | 12/2003 | Al-Ali et al. | |
| 6,678,543 | B2 | | 1/2004 | Diab et al. | |
| 6,684,090 | B2 | | 1/2004 | Ali et al. | |
| 6,684,091 | B2 | | 1/2004 | Parker | |
| 6,697,656 | B1 | | 2/2004 | Al-Ali | |
| 6,697,658 | B2 | | 2/2004 | Al-Ali | |
| RE38,476 | E | | 3/2004 | Diab et al. | |
| 6,699,194 | B1 | | 3/2004 | Diab et al. | |
| 6,711,424 | B1 | | 3/2004 | Fine et al. | |
| 6,714,804 | B2 | | 3/2004 | Al-Ali et al. | |
| RE38,492 | E | | 4/2004 | Diab et al. | |
| 6,721,585 | B1 | | 4/2004 | Parker | |
| 6,725,075 | B2 | | 4/2004 | Al-Ali | |
| 6,731,963 | B2 | | 5/2004 | Finarov et al. | |
| 6,735,459 | B2 | | 5/2004 | Parker | |
| 6,745,060 | B2 | | 6/2004 | Diab et al. | |
| 6,760,607 | B2 | | 7/2004 | Al-Ali | |
| 6,770,028 | B1 | | 8/2004 | Ali et al. | |
| 6,771,994 | B2 | | 8/2004 | Kiani et al. | |
| 6,782,276 | B1 | | 8/2004 | Lam et al. | |
| 6,792,300 | B1 | | 9/2004 | Diab et al. | |
| 6,804,002 | B2 | | 10/2004 | Fine et al. | |
| 6,813,511 | B2 | | 11/2004 | Diab et al. | |
| 6,816,741 | B2 | | 11/2004 | Diab | |
| 6,822,564 | B2 | | 11/2004 | Al-Ali | |
| 6,826,419 | B2 | | 11/2004 | Diab et al. | |
| 6,830,711 | B2 | | 12/2004 | Mills et al. | |
| 6,850,787 | B2 | | 2/2005 | Weber et al. | |
| 6,850,788 | B2 | | 2/2005 | Al-Ali | |

| | | | |
|---|---|---|---|
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin, IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 2002/0077535 | A1 | 6/2002 | Finarov et al. |
| 2004/0116788 | A1 | 6/2004 | Chernoguz et al. |
| 2004/0176671 | A1 | 9/2004 | Fine et al. |
| 2004/0225205 | A1 | 11/2004 | Fine et al. |
| 2004/0249252 | A1 | 12/2004 | Fine et al. |

FOREIGN PATENT DOCUMENTS

| | | |
|---|---|---|
| WO | WO 90/04353 | 5/1990 |
| WO | WO 92/17765 | 10/1992 |
| WO | WO 93/20745 | 10/1993 |
| WO | WO 96/39926 | 12/1996 |

OTHER PUBLICATIONS

Landowne, Milton, "A Method Using Induced Waves to Study Pressure Propagation in Human Arteries", *Circulation Research*, Nov. 1957, pp. 594-601.

OrSense "Overview of OrSense Technology," http://www.orsense.com/main/siteNew/?page=3, 1 page downloaded and printed from the World Wide Web on Jul. 26, 2005.

OrSense "FAQs," http://www.orsense.com/main/siteNew/?page=10, 3 pages downloaded and printed from the World Wide Web on Jul. 26, 2005.

OrSense "OrSense Advantages in the Hemoglobin Monitoring Market," http://www.orsense.com/main/siteNew/?page=25, 2 pages downloaded and printed from the World Wide Web on Jul. 26, 2005.

OrSense "Overview of Hemoglobin Monitoring," http://www.orsense.com/main/siteNew/?page=6, 1 page downloaded and printed from the World Wide Web on Jul. 26, 2005.

OrSense "Desktop Blood Monitor," http://www.orsense.com/main/siteNew/?page=22, 2 pages downloaded and printed from the World Wide Web on Jul. 26, 2005.

OrSense "Clinical Blood Monitor," http://www.orsense.com/main/siteNew/?page=23, 2 pages downloaded and printed from the World Wide Web on Jul. 26, 2005.

OrSense http://www.orsense.com/main/siteNew/?page=17, 2 pages downloaded and printed from the World Wide Web on Jul. 26, 2005.

Squire, J.R., "An Instrument for Measuring the Quality of Blood and Its Degree of Oxygenation in Web of the Hand", *Clinical Science*, vol. 4, pp. 331-339, 1940.

Wood, Earl H. et al., "Photoelectric Determination of Arterial Oxygen Saturation in Man", *Arterial Oxygen Saturation in Man*, pp. 387-401, 1948.

* cited by examiner

ACTIVE PULSE BLOOD CONSTITUENT MONITORING

Matter enclosed in heavy brackets [ ] appears in the original patent but forms no part of this reissue specification; matter printed in italics indicates the additions made by reissue.

CROSS-REFERENCE TO RELATED APPLICATIONS

*Notice: More than one reissue application has been filed for the reissue of U.S. Pat. No. 7,239,905. The reissue applications are application Ser. No. 12/497,517 (the present application) and Ser. No. 13/047,740 (continuation of present application), both of which are reissues of U.S. Pat. No. 7,239,905.*

This application is a continuation of U.S. patent application Ser. No. 09/706,965, filed Nov. 6, 2000, now U.S. Pat. No. 6,931,268, issued Aug. 16, 2005, which is a continuation of U.S. patent application Ser. No. 09/190,719, filed Nov. 12, 1998, now U.S. Pat. No. 6,151,516, issued Nov. 21, 2000, which is a continuation of U.S. patent application Ser. No. 08/843,863, filed Apr. 17, 1997, now U.S. Pat. No. 5,860,919, issued Jan. 19, 1999, which is a continuation of U.S. patent application Ser. No. 08/482,071, filed Jun. 7, 1995, now U.S. Pat. No. 5,638,816, issued Jun. 17, 1997. The present application incorporates the foregoing disclosures herein by reference.

BACKGROUND OF THE INVENTION

1. Field of the Invention

The present invention relates to noninvasive systems for monitoring blood glucose and other difficult to detect blood constituent concentrations, such as therapeutic drugs, drugs of abuse, carboxyhemoglobin, Methemoglobin, cholesterol.

2. Description of the Related Art

In the past, many systems have been developed for monitoring blood characteristics. For example, devices have been developed which are capable of determining such blood characteristics as blood oxygenation, glucose concentration, and other blood characteristics. However, significant difficulties have been encountered when attempting to determine blood glucose concentration accurately using noninvasive blood monitoring systems such as by means of spectroscopic measurement.

The difficulty in determining blood glucose concentration accurately may be attributed to several causes. One of the significant causes is that blood glucose is typically found in very low concentrations within the bloodstream (e.g., on the order of 100 to 1,000 times lower than hemoglobin) so that such low concentrations are difficult to detect noninvasively, and require a very high signal-to-noise ratio. Additionally, with spectroscopic methods, the optical characteristics of glucose are very similar to those of water which is found in a very high concentration within the blood. Thus, where optical monitoring systems are used, the optical characteristics of water tend to obscure the characteristics of optical signals due to glucose within the bloodstream. Furthermore, since each individual has tissue, bone and unique blood properties, each measurement typically requires calibration for the particular individual.

In an attempt to accurately measure blood glucose levels within the bloodstream, several methods have been used. For example, one method involves drawing blood from the patient and separating the glucose from the other constituents within the blood. Although fairly accurate, this method requires drawing the patient's blood, which is less desirable than noninvasive techniques, especially for patients such as small children or anemic patients. Furthermore, when blood glucose monitoring is used to control the blood glucose level, blood must be drawn three to six times per day, which may be both physically and psychologically traumatic for a patient. Other methods contemplate determining blood glucose concentration by means of urinalysis or some other method which involves pumping or diffusing body fluid from the body through vessel walls or using other body fluids such as tears or sweat. However, such an analysis tends to be less accurate than a direct measurement of glucose within the blood, since the urine, or other body fluid, has passed through the kidneys (or skin in the case of sweat). This problem is especially pronounced in diabetics. Furthermore, acquiring urine and other body fluid samples is often inconvenient.

As is well known in the art, different molecules, typically referred to as constituents, contained within the medium have different optical characteristics so that they are more or less absorbent at different wavelengths of light. Thus, by analyzing the characteristics of the fleshy medium containing blood at different wavelengths, an indication of the composition of the blood in the fleshy medium may be determined.

Spectroscopic analysis is based in part upon the Beer-Lambert law of optical characteristics for different elements. Briefly, Beer-Lambert's law states that the optical intensity of light through any medium comprising a single substance is proportional to the exponent of the product of path length through the medium times the concentration of the substance within the medium times the extinction coefficient of the substance. That is, $$I=I_o e^{-(pl*c*\epsilon)} \quad (1)$$

where pl represents the path length through the medium, c represents the concentration of the substance within, the medium, $\epsilon$ represents the absorbtion (extinction) coefficient of the substance and $I_o$ is the initial intensity of the light from the light source. For optical media which have several constituents, the optical intensity of the light received from the illuminated medium is proportional to the exponent of the path length through the medium times the concentration of the first substance times the optical absorption coefficient associated with the first substance, plus the path length times the concentration of the second substance times the optical absorption coefficient associated with the second substance, etc. That is, $$I=I_o e^{-(pl*c1*\epsilon 1+pl*c2*\epsilon 2+etc.)} \quad (2)$$

where $\epsilon_n$ represents the optical absorption (extinction) coefficient of the $n^{th}$ constituent and $c_n$ represents the concentration of the $n^{th}$ constituent.

SUMMARY OF THE INVENTION

Due to the parameters required by the Beer-Lambert law, the difficulties in detecting glucose concentration arise from the difficulty in determining the exact path length through a medium (resulting from transforming the multi-path signal to an equivalent single-path signal), as well as difficulties encountered due to low signal strength resultant from a low concentration of blood glucose. Path length through a medium such as a fingertip or earlobe is very difficult to determine, because not only are optical wavelengths absorbed differently by the fleshy medium, but also the signals are scattered within the medium and transmitted through different paths. Furthermore, as indicated by the above equation (2), the measured signal intensity at a given wavelength does not vary linearly with respect to the path length. Therefore, variations in path length of multiple paths of light through the medium do not result in a linear averaging of the multiple path lengths. Thus, it is often very difficult to determine an exact path length through a fingertip or earlobe for each wavelength.

In conventional spectroscopic blood constituent measurements, such a blood oxygen saturation, light is transmitted at various wavelengths through the fleshy medium. The fleshy medium (containing blood) attenuates the incident light and the detected signal can be used to calculate certain saturation values. In conventional spectroscopic blood constituent measurements, the heart beat provides a minimal modulation to the detected attenuated signal in order to allow a computation based upon the AC portion of the detected signal with respect to the DC portion of the detected signal, as disclosed in U.S. Pat. No. 4,407,290. This AC/DC operation normalizes the signal and accounts for variations in the pathlengths, as well understood in the art.

However, the natural heart beat generally provides approximately a 1-10% modulation (AC portion of the total signal) of the detected signal when light is transmitted through a patient's digit or the like. That is, the variation in attenuation of the signal due to blood may be only 1% of the total attenuation (other attenuation being due to muscle, bone, flesh, etc.). In fact, diabetes patients typically have even lower modulation (e.g., 0.01-0.1%). Therefore, the attenuation variation (AC portion of the total attenuation) due to natural pulse can be extremely small. In addition, the portion of the pulse modulation which is due to glucose is roughly only 9% of the pulse (approximately $1/11$) at a wavelength of 1330-1340 nm where glucose absorbs effectively. Furthermore, to resolve glucose from 5 mg/dl to 1005 mg/dl in increments or steps of 5 mg/dl, requires resolution of $1/200$ of the 9% of the modulation which is due to glucose. Accordingly, by way of three different examples—one for a healthy individual, one for a diabetic with a strong pulse, and one for a diabetic with a weak pulse—for absorption at 1330 nm, the system would require resolution as follows.

EXAMPLE 1

Healthy Individuals where Natural Pulse Provides Attenuation Modulation of 1% at 1330 nm a. Natural modulation due to pulse is approximately 1% ($1/100$).
b. Portion of natural modulation due to glucose is approximately 9% ($1/11$).
c. To resolve glucose from 5-1005 mg/dl requires resolution of $1/200$ (i.e., there are 200, 5 mg/dl steps between 5 and 1005 mg/dl).

Required Total Resolution is product of a-c: $1/100*1/11*1/200=1/220{,}000$

EXAMPLE 2

Diabetic where Natural Pulse Provides Attenuation Modulation of 0.1% at 1330 nm a. Natural modulation due to pulse approximately 0.1% ($1/1000$).
b. Portion of natural modulation due to glucose is approximately 9% ($1/11$)
c. To resolve glucose from 5-1005 mg/dl requires resolution of $1/200$.

Required total resolution is product of a-c: $1/100*1/11*1/200=1/220{,}000$

EXAMPLE 3

Diabetic where Natural Pulse Provides Attenuation Modulation of 0.01% a. Natural modulation due to pulse approximately 0.01% ($1/10{,}000$).
b. Portion of natural modulation due to glucose is approximately 9% ($1/11$).
c. To resolve glucose from 5-1005 mg/dl requires resolution of $1/200$.

Required total resolution is product of a-c: $1/10{,}000*1/11*1/200=1/220{,}000$ As seen from the above three examples which provide the range of modulation typically expected among human patients, the total resolution requirements range from 1 in 220,000 to 1 in 22,000,000 in order to detect the attenuation which is due to glucose based on the natural pulse for the three examples. This is such a small portion that accurate measurement is very difficult. In most cases, the noises accounts for a greater portion of the AC portion (natural modulation due to pulse) of the signal than the glucose, leaving glucose undetectable. Even with state of the art noise reduction processing as described in U.S. patent application Ser. No. 08/249,690, filed May 26, 1994, now U.S. Pat. No. 5,482,036, signals may be resolved to a level of approximately $1/250{,}000$. This is for an 18-bit system. With a 16-bit system, resolution is approximately $1/65{,}000$. In addition, LEDs are often noisy such that even if resolution in the system is available to $1/250{,}000$, the noise from the LEDs leave glucose undetectable.

To overcome these obstacles, it has been determined that by actively inducing a change in the flow of blood in the medium under test such that the blood flow varies in a controlled manner periodically, modulation can be obtained such that the portion of the attenuated signal due to blood becomes a greater portion of the total signal than with modulation due to the natural pulse. This leads to the portion of total attenuation due to glucose in the blood being a greater portion of the total signal. In addition, the signal can be normalized to account for factors such as source brightness, detector responsiveness, tissue or bone variation. Changes in blood flow can be induced in several ways, such as physically perturbing the medium under test or changing the temperature of the medium under test. In the present embodiment, by actively inducing a pulse, a 10% modulation in attenuation ($1/10$ of the total attenuation) is obtained, regardless of the patient's natural pulse modulation (whether or not the patient is diabetic). Accordingly, at 1330 nm with actively induced changes in blood flow, the resolution required is $1/10*1/11*1/200$ or $1/22{,}000$ (where $1/10$ is the active pulse attenuation modulation (the modulation obtained by induced blood flow changes), $1/11$ is the portion of the modulation due to glucose, and $1/200$ the resolution required to obtain glucose in 5 mg/dl increments from 5-1005 mg/dl). As will be understood from the discussion above, such resolution can be obtained, even in a 16 bit system. In addition, the resolution is obtainable beyond the noise floor, as described herein.

In conventional blood constituent measurement through spectroscopy, perturbation of the medium under test has been avoided because oxygen (the most commonly desired parameter) is not evenly dispersed in the arterial and venous blood. Therefore, perturbation obscures the ability to determine the arterial oxygen saturation because that venous and arterial blood become intermingled. However, glucose is evenly dispersed in blood fluids, so the mixing of venous and arterial blood and interstitial fluids should have no significant effect on the glucose measurements. It should be appreciated that this technique will be effective for any substance evenly dispersed in the body fluids (e.g., blood, interstitial fluids, etc.).

One aspect of the present invention involves a system for non-invasively monitoring a blood constituent concentration in a living subject. The system comprises a light source which emits radiation at a plurality of wavelengths and an active pulse inducement device which, independent of the natural flow of blood in the fleshy medium, causes a periodic change in the volume of blood in the fleshy medium. An optical detector positioned to detect light which has propagated through the fleshy medium is configured to generate an output signal indicative of the intensity of the radiation after attenuation through the fleshy medium. A signal processor responds to the output signal to analyze the output signal to extract portions of the signal due to optical characteristics of the blood to determine the concentration of the constituent within the subject's bloodstream.

In one embodiment, of the system further comprises a receptacle which receives the fleshy medium, the receptacle further having an inflatable bladder.

In one embodiment, the system has a temperature variation element in the receptacle, the temperature variation element varies (e.g., increases) the temperature of the fleshy medium in order to induce a change (e.g., increase) in the flow of blood in the fleshy medium.

Another aspect of the present invention involves a system for non-invasively monitoring blood glucose concentration within a patient's bloodstream. A light source emits optical radiation at a plurality of frequencies, and a sensor receives a fleshy medium of the patient, the fleshy medium having flowing blood. A fluid (e.g., blood and interstitial fluids) volume change inducement device causes a cyclic change in the volume of blood in the fleshy medium. An optical detector positioned to receive the optical radiation after transmission through a portion of the fleshy medium responds to the detection of the optical radiation to generate an output signal indicative of the intensity of the optical radiation. A signal processor coupled to the detector receives the output signal, and responds to the output signal to generate a value representative of the glucose concentration in the blood of the patient.

Yet another aspect of the present invention involves a method of non-invasively determining a concentration of a blood constituent. The method comprises a plurality of steps. Optical radiation is transmitted through a medium having flowing fluid, wherein the fluid has a concentration of the fluid constituent. A periodic change in the volume of the fluid in the medium is actively induced. The optical optical radiation after transmission through at least a portion of the medium is detected and a signal indicative of the optical characteristics of the medium is generated. The signal is analyzed to determine the concentration of the blood constituent. In one embodiment, the fluid constituent comprises blood glucose.

A further aspect of the present invention involves a method of actively varying the attenuation of optical radiation due to blood in a fleshy medium. The method comprises a plurality of steps. Optical radiation is transmitted through the fleshy medium. A periodic change in the volume of blood is actively influenced in the medium The optical radiation is detected after attenuation through the fleshy medium and an output signal indicative of the intensity of the attenuated signal is generated.

DETAILED DESCRIPTION OF THE PREFERRED EMBODIMENT

Figure 1:
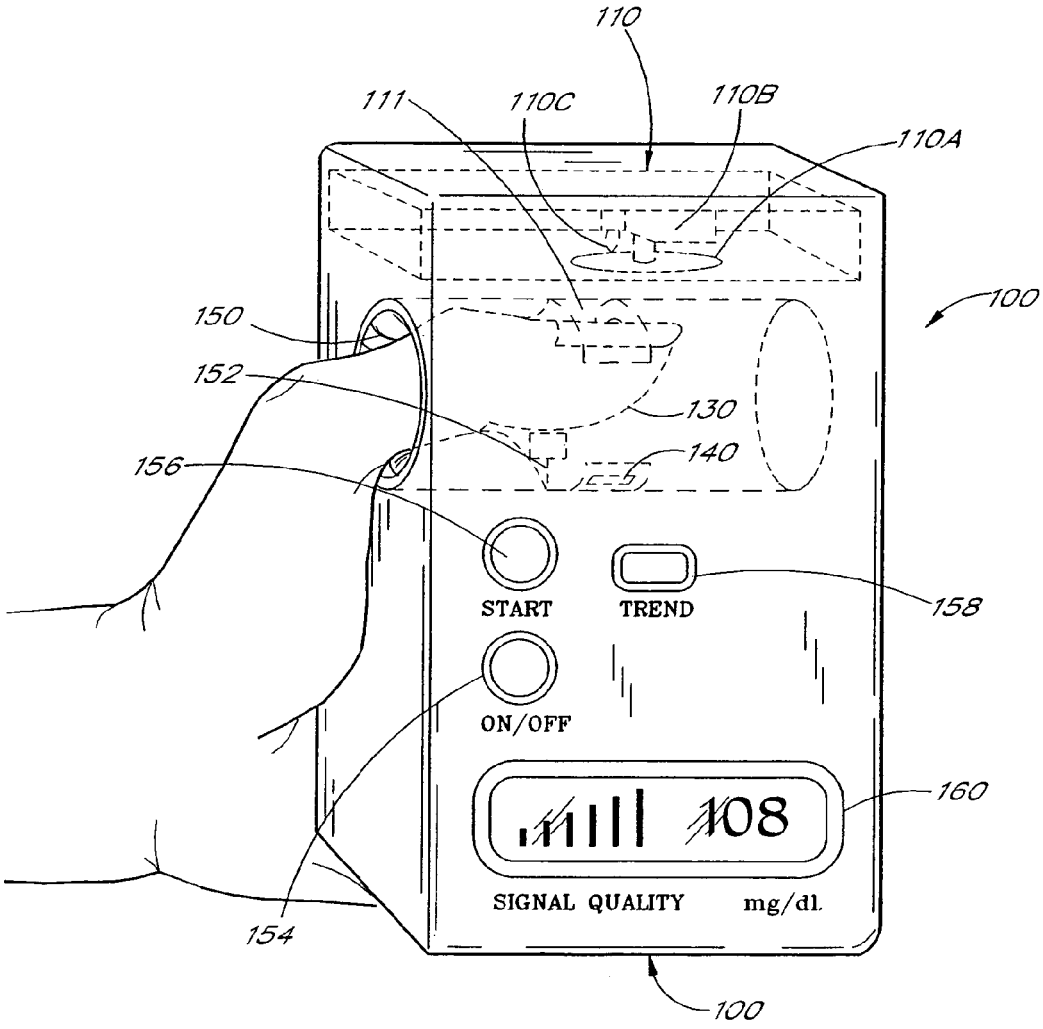
FIG. 1 depicts an embodiment of a blood glucose monitor of the present invention.

FIG. 1 depicts one embodiment of a blood glucose monitor system 100 in accordance with the teachings of the present invention. The glucose monitor 100 of FIG. 1 has an emitter 110 such as light emitting diodes or a light with a filter wheel as disclosed in U.S. patent application Ser. No. 08/479,164, now U.S. Pat. No. 5,743,262 Masimo. 014A) entitled Blood Glucose Monitoring System, filed on the same day as this application, and assigned to the assignee of this application, which application is incorporated by reference herein.

The filter wheel with a broadband light is depicted in FIG. 1. This arrangement comprises a filter wheel 110A, a motor 110B, and a broadband light source 110C. Advantageously, this unit can be made relatively inexpensively as a replaceable unit. The filter wheel is advantageously made in accordance with U.S. patent application Ser. No. 08/486,798 now U.S. Pat. No. 5,760,910 entitled Optical Filter for Spectroscopic Measurement and Method of Producing the Optical Filter, filed on the same date as this application, and assigned to the assignee of this application, which application is incorporated herein by reference.

The monitor system 100 has a detector 140, such as a photodetector. The blood glucose monitor 100 also has a pressure inducing cuff 150 to physically squeeze a digit 130 in order to periodically induce a "pulse" in the fluid (i.e., actively vary the flow of fluid) in a digit 130. In other words, a device influences a change in the volume of blood in the digit or other fleshy medium. A window 111 is positioned to allow light from the emitter 110 to pass through the window 11 and transmit through the digit 130. This intentional active perturbation of the blood in the digit or medium under test is further referred to herein as an "active pulse." The blood glucose monitor also has a display 160 which may be used to indicate such parameters as glucose concentration and signal quality. Advantageously, the blood glucose monitor also has a power switch 154, a start switch 156 and a trend data switch 158.

Other methods of inducing a pulse are also possible. For instance, the fleshy medium under test, such as the patient's digit, could be perturbed with a pressure device 152 (depicted in dotted lines in FIG. 1). Other methods of inducing a pulse could be utilized such as temperature fluctuations or other physiological changes which result in a fluctuation (modulation) of blood volume through the fleshy medium. All external methods (as opposed to the natural heart beat) actively vary the blood volume in the medium under test are collectively referred to herein as inducing an "active pulse." In the present embodiment, 10% modulation in the total attenuation is obtained through the active induction of a pulse. The 10% modulation is selected as a level of minimal perturbation to the system. Too much perturbation of the medium will change the optical characteristics of the medium under test. For instance, with substantial modulation (e.g., 40-50%), the perturbation could impact scattering within the medium under test differently for different wavelengths, thus causing inaccurate measurements.

The pressure device 152, the cuff 150 and the use of temperature to induce a pulse in the fleshy medium are advantageous in that they can be used with minimal or no movement of the fleshy medium in the area through which light is transmitted. This is possible through inducing the pulse at a location proximal or distal from the area receiving the incident light. The advantage of minimal movement is that movement in the area of the fleshy medium under test causes variation in the detected signal other than due to the varying fluid volume (e.g., blood and interstitial fluid) flow. For instance, physical perturbation in the area of light transmission can cause changes in the light coupling to the medium under test resulting in variations in attenuation which are not due to changes in fluid volume in the area of light transmission. These other variations comprise additional noise that should be removed for accurate measurement.

Figure 2:
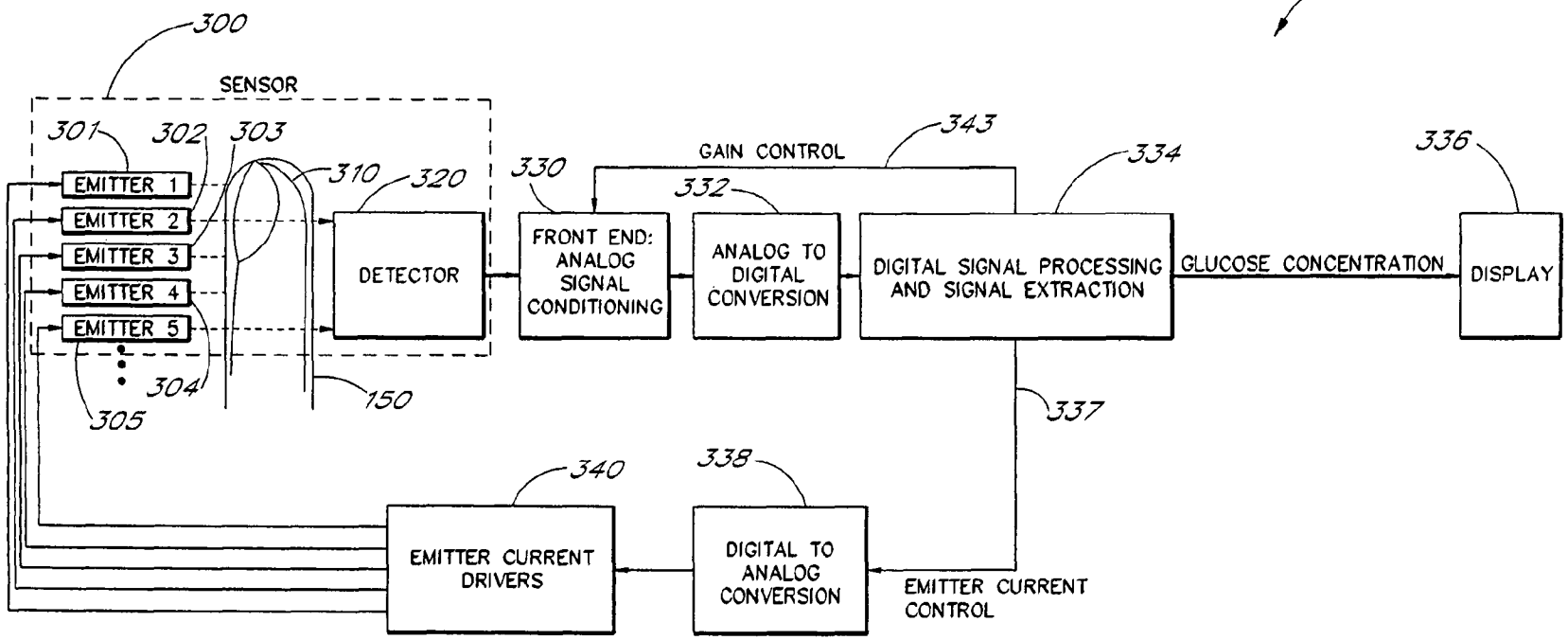
FIG. 2 depicts an example of a physiological monitor in accordance with the teachings of the present invention.
Figure 3:
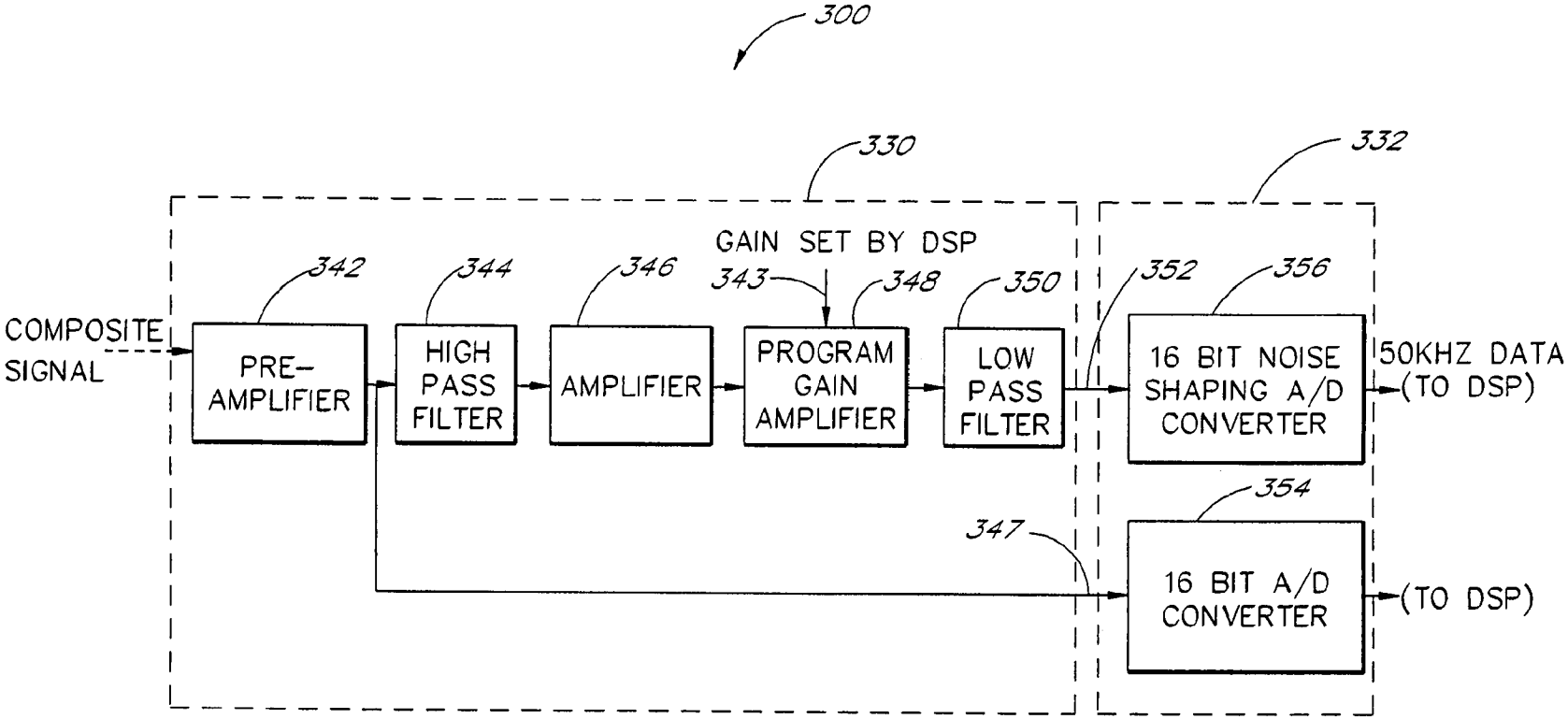
FIG. 3 illustrates the front end analog signal conditioning circuitry and the analog to digital conversion circuitry of the physiological monitor of FIG. 2.
Figure 4:
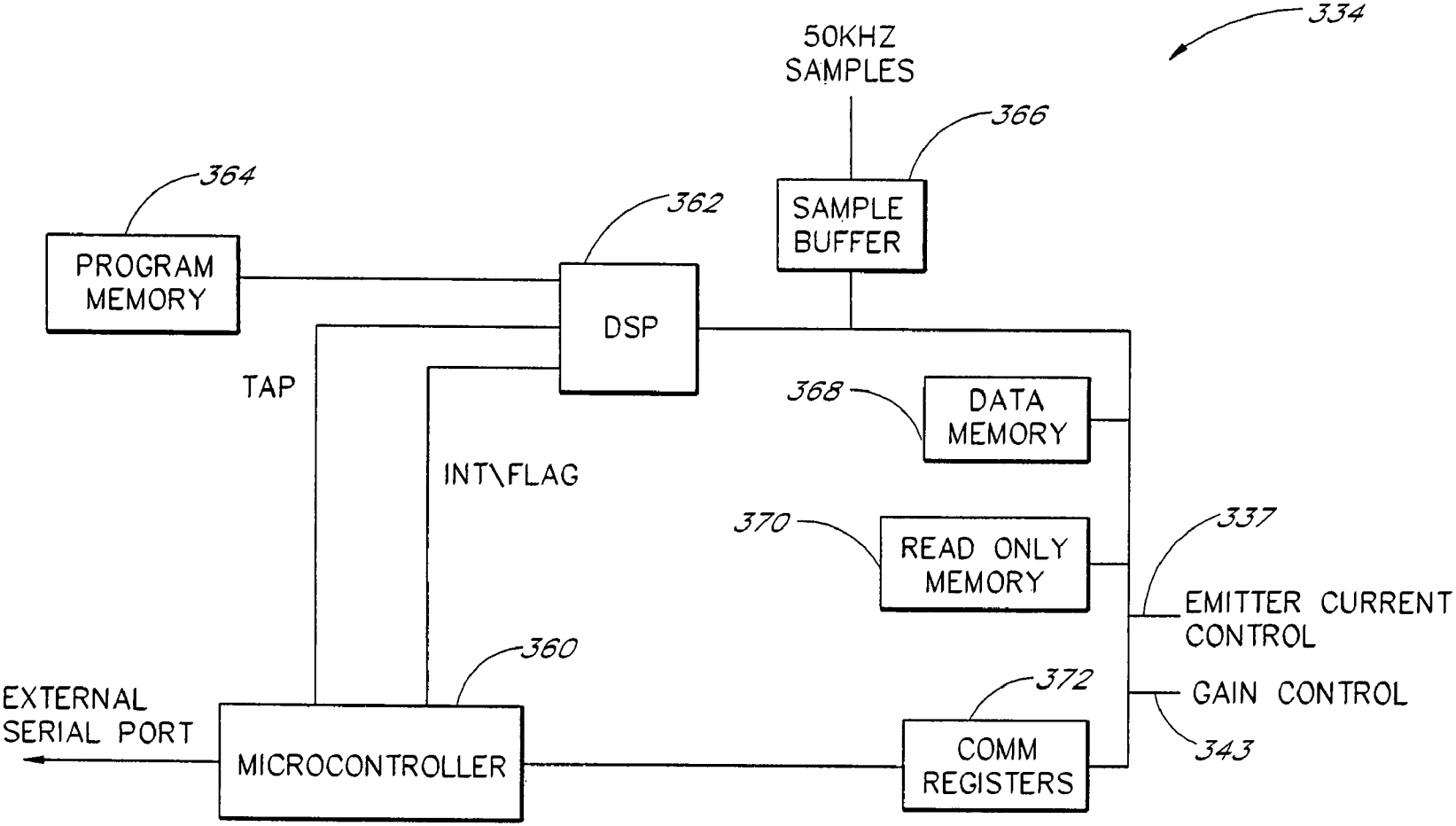
FIG. 4 illustrates further detail of the digital signal processing circuitry of FIG. 2.

FIGS. 2-4 depict a schematic block diagram of the blood glucose monitoring system 100 in accordance with the teachings of the present invention. FIG. 2 illustrates a general hardware block diagram. A sensor 300 has multiple light emitters 301-305 such as LED's. In the present embodiment, each LED 301-305 emits light at a different wavelength.

Figure 9:
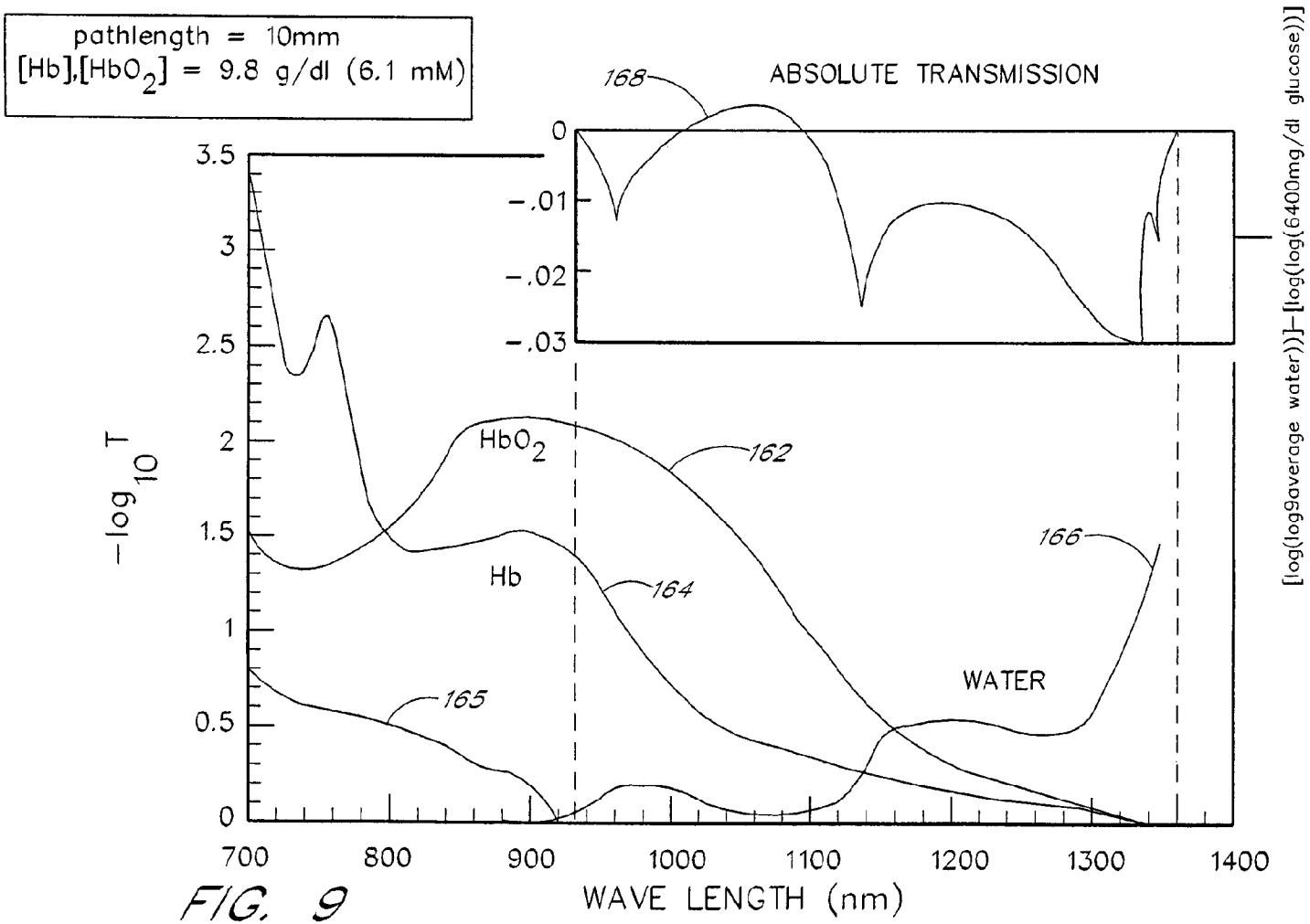
FIG. 9 illustrates the extinction coefficient versus wavelength for several blood constituents.

As well understood in the art, because Beer-Lambert's law contains a term for each constituent which attenuates the signal, one wavelength is provided for each constituent which is accounted for. For increased precision, the wavelengths are chosen at points where attenuation for each particular constituent is the greatest and attenuation by other constituents is less significant. FIG. 9 depicts the extinction coefficient on a log scale vs. wavelength for principal blood constituents. The curve 162 represents the extinction coefficient for oxyhemoglobin; the curve 164 represents the extinction coefficient for hemoglobin; the curve 165 represents the extinction coefficient for carboxyhemoglobin; and the curve 166 represents the extinction coefficient for water. Depicted on the same horizontal axis with a different vertical axis is a curve 168 which represents the extinction coefficient for glucose in body fluids. It should be noted that the curve 168 is placed above the other curves and is greatly amplified, and therefore is not to scale on the graph. If the glucose curve were graphed on the same scale as the other constituents, it would simply appear as flat line at '0' on the vertical axis in the wavelength range from 900-1400 mm. The provision for a seperate vertical axis provides for amplification in order to illustrate at which wavelengths glucose attenuates the most in the range of interest. The vertical axis for the glucose curve 168 also represents a different value. In FIG. 9, the vertical axis for the curve 168 is in terms of the absolute transmission on the following log scale:

[log(log(average water))]−[log(log(6400 mg/dl glucose))]

However, for purposes of choosing appropriate wavelengths, the scale is of less significance that the points at which Glucose and the other constituents show good attenuation and the attenuation is not totally obscured by other constituents in the medium.

In the present embodiment, advantageous wavelengths for the emitters 301-305 (or to obtain with the filter wheel and signal processing) are 660 nm (good attenuation hemoglobin), 905 nm (good attenuation from oxyhemoglobin), 1270 nm (good attenuation by water, and little attenuation by other constituents) 1330-1340 nm (good attenuation due to Glucose in the area of the graph labelled A of FIG. 9, not totally obscured by the attenuation due to water), and 1050 nm (an additional point for good attenuation from Glucose). The use of two wavelengths to account for glucose attenuation provides overspecification of the equations. Overspecification of the equations discussed below increases resolution. Additional wavelengths to account for other constituents such as fats and proteins or others could also be included. For instance, an additional wavelength at 1100 nm could be added (good attenuation from-proteins) and 920 nm (good attenuation from fats). Another constituent often of interest is carboxyhemoglobin. A wavelength for carboxyhemoglobin is advantageously selected at 700-730 nm.

In addition to using multiple precise LEDs, an optical spectroscopic system for generating the optical characteristics over many wavelengths can be used. Such a device is disclosed in U.S. patent application Ser. No. 08/479,164, entitled Blood Glucose Monitoring System, filed on the same day as this application, and assigned to the assignee of this application.

The sensor 300 further comprises a detector 320 (e.g., a photodetector), which produces an electrical signal corresponding to the attenuated light energy signals. The detector 320 is located so as to receive the light from the emitters 301-305 after it has propagated through at least a portion of the medium under test. In the embodiment depicted in FIG. 2, the detector 320 is located opposite the LED's 301-305. The detector 320 is coupled to front end analog signal conditioning circuity 330.

The front end analog signal conditioning circuitry 330 has outputs coupled to analog to digital conversion circuit 332. The analog to digital conversion circuitry 332 has outputs coupled to a digital signal processing system 334. The digital signal processing system 334 provides the desired parameter as an output for a display 336. The display 336 provides a reading of the blood glucose concentration.

The signal processing system also provides an emitter current control output 337 to a digital-to-analog converter circuit 338 which provides control information for emitter drivers 340. The emitter drivers 340 couple to the emitters; 301-305. The digital signal processing system 334 also provides a gain control output 342 for the front end analog signal conditioning circuitry 330.

Figure 2A:
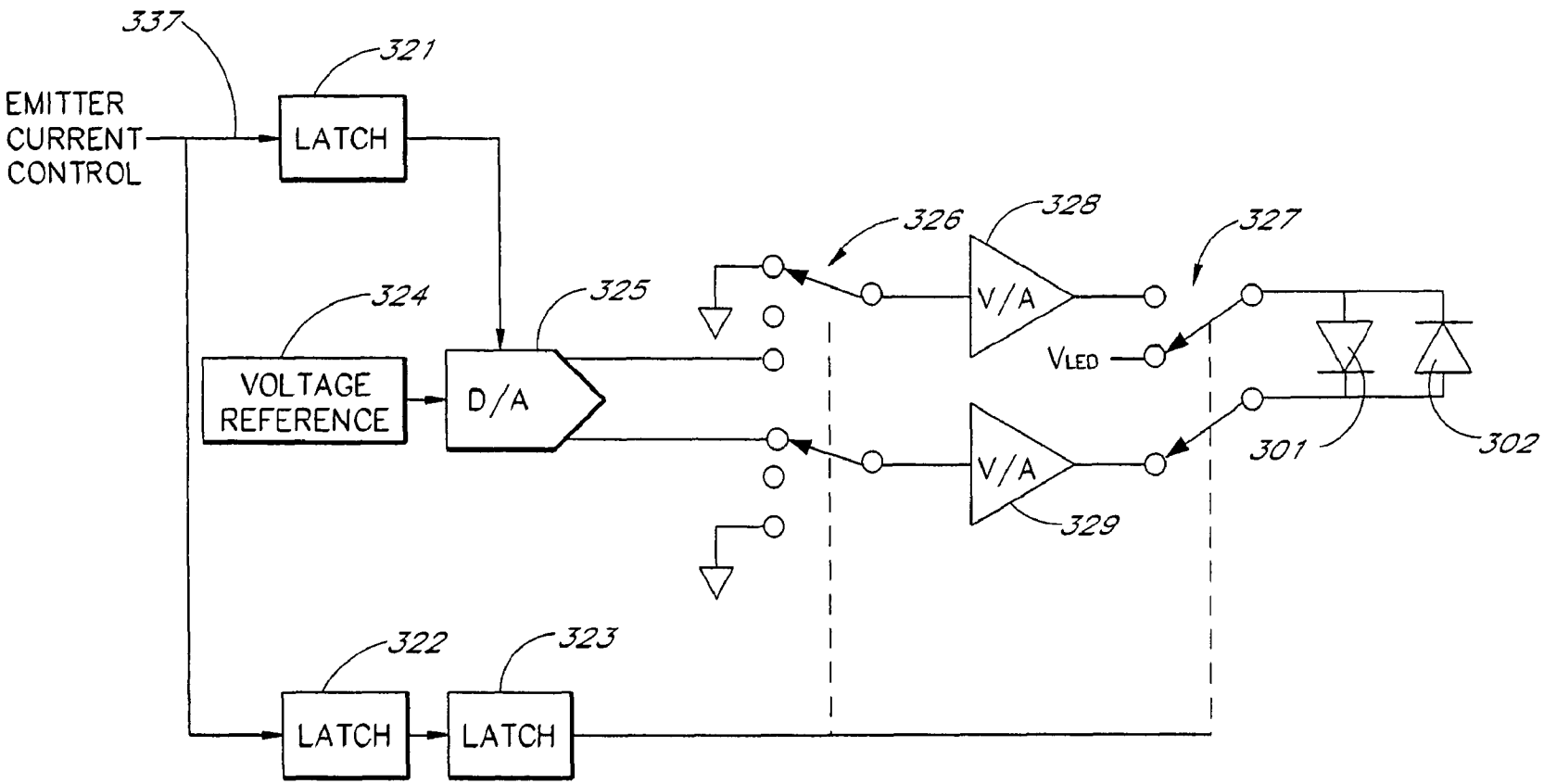
FIG. 2A illustrates an example of a low noise emitter current driver with accompanying digital to analog converter.

FIG. 2A illustrates a preferred embodiment for the emitter drivers 340 and the digital to analog conversion circuit 338. The driver depicted in FIG. 2a is depicted for two LEDs coupled back-to-back. However, additional LEDs (preferably coupled back-to-back to conserve connections) can be coupled to the D/A converter 325 through additional multiplexing circuitry (not shown). As depicted in FIG. 2A, the driver comprises first and second input latches 321, 322, a synchronizing latch 323, a voltage reference 324, a digital to analog conversion circuit 325, first and second switch banks 326, 327, first and second voltage to current converters 328, 329 and the LED emitters 301, 302 corresponding to the LED emitters 301-302 of FIG. 2.

The preferred driver depicted in FIG. 2A is advantageous in that much of the noise in the blood glucose system 100 of FIG. 2 is caused by the LED emitters 301-305. Therefore, the emitter driver circuit of FIG. 2A is designed to minimize the noise from the emitters 301-305. The first and second input latches 321, 324 are connected directly to the DSP bus. Therefore, these latches significantly minimize the bandwidth (resulting in noise) present on the DSP bus which passes through to the driver circuitry of FIG. 2A. The output of the first and second input latches only changes when these latches detect their address on the DSP bus. The first input latch receives the setting for the digital to analog converter circuit 325. The second input latch receives switching control data for the switch banks 326, 327. The synchronizing latch accepts the synchronizing pulses which maintain synchronization between the activation of emitters 301, 302 (and the other emitters 303-305 not depicted in FIG. 2a) and the analog to digital conversion circuit 332.

The voltage reference is also chosen as a low noise DC voltage reference for the digital to analog conversion circuit 325. In addition, in the present embodiment, the voltage reference has an lowpass output filter with a very low corner frequency (e.g., 1 Hz in the present embodiment). The digital to analog converter 325 also has a lowpass filter at its output with a very low corner frequency (e.g., 1 Hz). The digital to analog converter provides signals for each of the emitters 301, 302 (and the remaining emitters 303-305, not depicted in FIG. 2a).

In the present embodiment, the output of the voltage to current converters 328, 329 are switched such that with the emitters 301, 302 connected in back-to-back configuration, only one emitter is active an any given time. A refusal position for the switch 326 is also provided to allow the emitters 301 and 302 to both be off when one of the other emitters 303-305 is on with a similar switching circuit. In addition, the voltage to current converter for the inactive emitter is switched off at its input as well, such that it is completely deactivated. This reduces noise from the switching and voltage to current conversion circuitry. In the present embodiment, low noise voltage to current converters are selected (e.g., Op 27 Op Amps), and the feedback loop is configured to have a low pass filter to reduce noise. In the present embodiment, the low pass filtering function of the voltage to current converter 328, 329 has a corner frequency just above the switching speed for the emitters. Accordingly, the preferred driver circuit of FIG. 2a, minimizes the noise of the emitters 301, 302.

As represented in FIG. 2, the light emitters 301-305 each emits energy which is absorbed by the finger 310 and received by the detector 320. The detector 320 produces an electrical signal which corresponds to the intensity of the light energy striking the photodetector 320. The front end analog signal conditioning circuitry 330 receives the intensity signals and filters and conditions these signals as further described below for further processing. The resultant signals are provided to the analog-to-digital conversion circuitry 332 which converts the analog signals to digital signals for further processing by the digital signal processing system 334. The digital signal processing system 334 utilizes the signals in order to provide blood glucose concentration. In the present embodiment, the output of the digital signal processing system 334 provides a value for glucose saturation to the display 336. Advantageously, the signal processing system 334 also store data over a period of time in order to generate trend data and perform other analysis on the data over time.

The digital signal processing system 334 also provides control for driving the light emitters 301-305 with an emitter current control signal on the emitter current control output 337. This value is a digital value which is converted by the digital-to-analog conversion circuit 338 which provides a control signal to the emitter current drivers 340. The emitter current drivers 340 provide the appropriate current drive for the emitters 301-305.

In the present embodiment, the emitters 301-305 are driven via the emitter current driver 340 to provide light transmission with digital modulation at 625 Hz. In the present embodiment, the light emitters 301-305 are driven at a power level which provides an acceptable intensity for detection by the detector and for conditioning by the front end analog signal conditioning circuitry 330. Once this energy level is determined for a given patient by the digital signal processing system 334, the current level for the emitters is maintained constant. It should be understood, however, that the current could be adjusted for changes in the ambient room light and other changes which would effect the voltage input to the front end analog signal conditioning circuitry 330. In the present invention, light emitters are modulated as follows: for one complete 625 Hz cycle for the first wavelength, the first emitter 301 is activated for the first tenth of the cycle, and off for the remaining nine-tenths of the cycle; for one complete 625 Hz second wavelength cycle, the second light emitter 302 is activated for the one tenth of the cycle and off for the remaining nine-tenths cycle; for one 625 Hz third wavelength cycle, the third light emitter 303 is activated for one tenth cycle and is off for the remaining nine-tenths cycle; for one 625 Hz fourth wavelength cycle, the fourth light emitter 304 is activated for one tenth cycle and is off for the remaining nine-tenths cycle; and for one 625 Hz fifth wavelength cycle, the fifth light emitter 305 is activated for one tenth cycle and is off for the remaining nine-tenths cycle. In order to receive only one signal at a time, the emitters are cycled on and off alternatively, in sequence, with each only active for a tenth cycle per 625 Hz cycle and a tenth cycle separating the active times.

Figure 13:
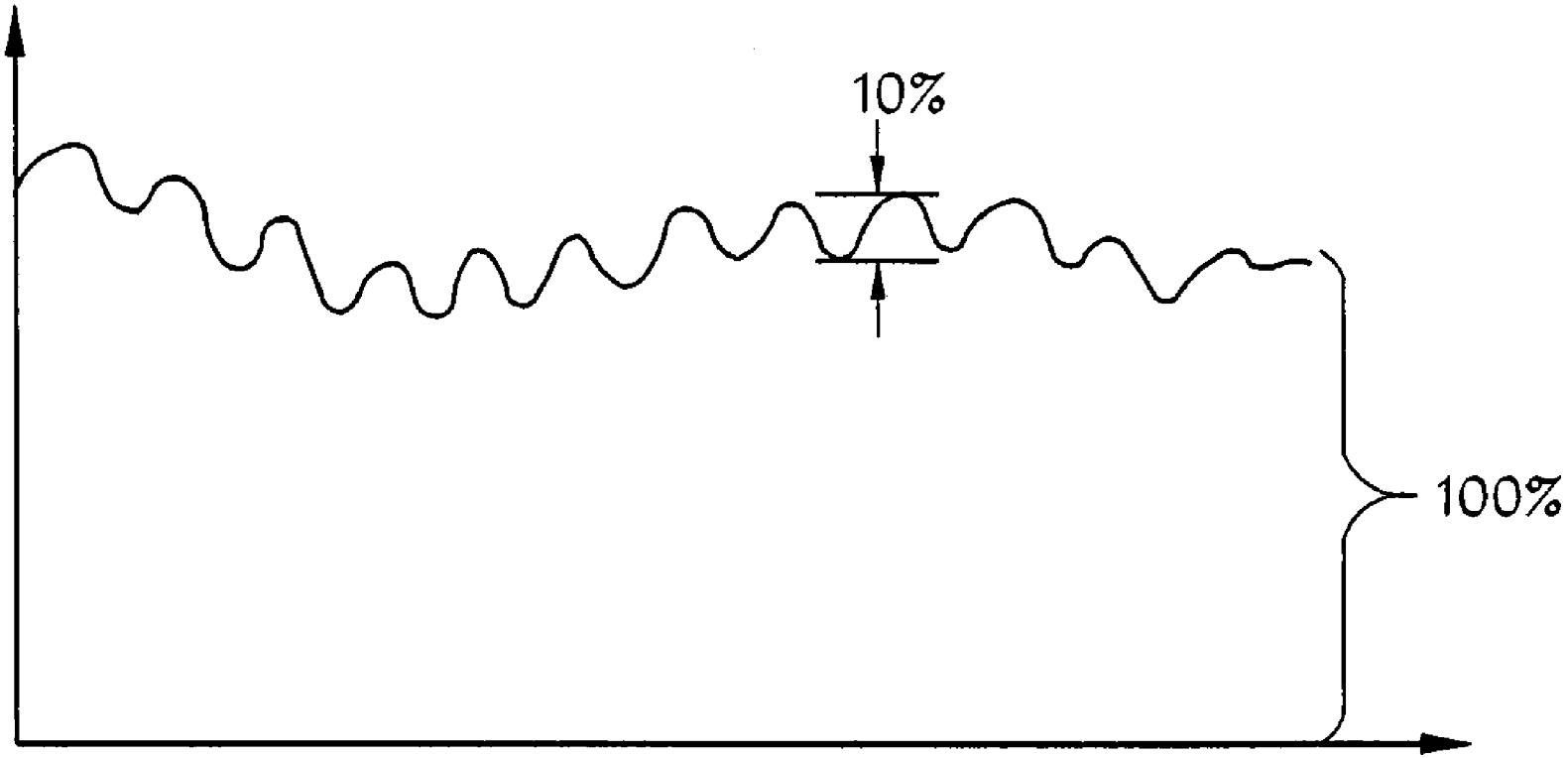
FIG. 13 depicts an example of the an active pulse signal where the modulation is 10% of the entire attenuation through the finger.

The light signal is attenuated (amplitude modulated) by the blood (with the volume of blood changing through cyclic active pulse in the present embodiment) through the finger 310 (or other sample medium). In the present embodiment, the fingertip 130 is physiologically altered on a periodic basis by the pressure device 150 (or the active pulse device) so that approximately 10% amplitude modulation is achieved. That is, enough-pressure is applied to the fingertip 310 to evacuate a volume of body fluid such that the variation in the overall difference in optical attenuation observed between the finger tip 310 when full of blood and the finger tip 310 when blood is evacuated, is approximately 10%. For example, if the transmission of optical radiation through the fingertip 310 is approximately 0.4%, then the fingertip 310 would have to be physiologically altered to evacuate enough blood so that the attenuation of the fingertip having fluid evacuated would be on the order to 0.36%. FIG. 13 depicts an example of the an active pulse signal where the modulation is 10% of the entire attenuation through the finger. The 10% is obtained by varying the volume of blood enough to obtain the cyclic modulation depicted in FIG. 13. As explained above, the 10% modulation is chosen as sufficient to obtain information regarding glucose concentrations, yet cause minimal perturbation to the system. Minimal perturbation is advantageous due to the optical variations caused by perturbing the system. The level of perturbation is advantageously below a level that causes significant variations in optical properties in the system, which variations affect different wavelengths differently.

In one advantageous embodiment, physiological altering of the fingertip 310 is accomplished by the application of periodic gentle pressure to the patient's finger 310 with the pressure cuff 150 (FIG. 1). The finger 310 could also be perturbed by the pressure device 152 (FIG. 1) or with temperature.

The modulation is performed at a selected rate. A narrow band pass filter may then be employed to isolate the frequency of interest. In the present embodiment, the modulation obtained through influencing an active pulse preferably occurs at a rate just above the normal heart rate (for instance, 4 Hz). In one embodiment, the system checks the heart rate and sets the active pulse rate such that it is above the natural heart rate, and also away from harmonics of the natural pulse rate. This allows for easy filtering with a very narrow band-pass filter with a center frequency of at the selected active pulse rate (e.g., 4 Hz or the rate automatically selected by the system to be away from the fundamental natural heart rate frequency and any harmonics to the fundamental frequency). However, a frequency in or below the range of normal heart rate could also be used. Indeed, in one embodiment, the frequency tracks the heart rate, in which case the active pulse operates in conjunction with the natural pulse to increase the change in volume of flow with each heart beat.

The attenuated (amplitude modulated) signal is detected by the photodetector 320 at the 625 Hz carrier frequency for each emitter. Because only a single photodetector is used, the photodetector 320 receives all the emitter signals to form a composite time division signal. In the present embodiment, a photodetector is provided which is a sandwich-type photodetector with a first layer which is transparent to infrared wavelengths but detects red wavelengths and a second layer which detects infrared wavelengths. One suitable photodetector is a K1713-05 photodiode made by Hamamatsu Corp. This photodetector provides for detection by the infrared layer of a relatively large spectrum of infrared wavelengths, as well as detection of a large spectrum of wavelengths in the red range by the layer which detects red wavelengths, with a single photodetector. Alternatively, multiple photodetectors could be utilized for the wavelengths in the system.

The composite time division signal is provided to the front analog signal conditioning circuitry 330. Additional detail regarding the front end analog signal conditioning circuitry 330 and the analog to digital converter circuit 332 is illustrated in FIG. 3. As depicted in FIG. 3, the front end circuity 300 has a preamplifier 342, a high pass filter 344, an amplifier 346, a programmable gain amplifier 348, and a low pass filter 350. The preamplifier 342 is a transimpedance amplifier that converts the composite current signal from the photodetector 320 to a corresponding voltage signal, and amplifies the signal. In the present embodiments, the preamplifier has a predetermined gain to boost the signal amplitude for ease of processing. In the present embodiment, the source voltages for the preamplifier 342 are −15 VDC and +15 VDC. As will be understood, the attenuated signal contains a component representing ambient light as well as the component representing the light at each wavelength transmitted by each emitter 301-305 as the case may be in time. If there is light in the vicinity of the sensor 300 other than from the emitters 301-305, this ambient light is detected by the photodetector 320. Accordingly, the gain of the preamplifier is selected in order to prevent the ambient light in the signal from saturating the preamplifier under normal and reasonable operating conditions.

The output of the preamplifier 342 couples as an input to the high pass filter 344. The output of the preamplifier also provides a first input 347 to the analog to digital conversion circuit 332. In the present embodiment, the high pass filter is a single-pole filter with a corner frequency of about ½-1 Hz. However, the corner frequency is readily raised to about 90 Hz in one embodiment. As will be understood; the 625 Hz carrier frequency of the emitter signals is well above a 90 Hz corner frequency. The high-pass filter 344 has an output coupled as an input to an amplifier 346. In the present embodiment, the amplifier 346 comprises a unity gain transimpedance amplifier. However, the gain of the amplifier 346 is adjustable by the variation of a single resistor. The gain of the amplifier 346 would be increased if the gain of the preamplifier 342 is decreased to compensate for the effects of ambient light.

The output of the amplifier 346 provides an input to a programmable gain amplifier 348. The programmable gain amplifier 348 also accepts a programming input from the digital signal processing system 334 on a gain control signal line 343. The gain of the programmable gain amplifier 348 is digitally programmable. The gain is adjusted dynamically at initialization or sensor placement for changes in the medium under test from patient to patient. For example, the signal from different fingers differs somewhat. Therefore, a dynamically adjustable amplifier is provided by the programmable gain amplifier 348 in order to obtain a signal suitable for processing.

The output of the programmable gain amplifier 348 couples as an input to a low-pass filter 350. Advantageously, the low pass filter 350 is a single-pole filter with a corner frequency of approximately 10 Khz in the present embodiment. This low pass filter provides antialiasing in the present embodiment.

The output of the low-pass filter 350 provides a second S input 352 to the analog-to-digital conversion circuit 332. FIG. 3 also depicts additional details of the analog-to-digital conversion circuit. In the present embodiment, the analog-to-digital conversion circuit 332 comprises a first analog-to-digital converter 354 and a second analog-to-digital converter 356. Advantageously, the first analog-to-digital converter 354 accepts signals from the first input 347 to the analog-to-digital conversion circuit 332, and the second analog to digital converter 356 accepts signals on the second input 352 to the analog-to-digital conversion circuitry 332.

In one advantageous embodiment, the first analog-to-digital converter 354 is a diagnostic analog-to-digital converter. The diagnostic task (performed by the digital signal processing system) is to read the output of the detector as amplified by the preamplifier 342 in order to determine if the signal is saturating the input to the high-pass filter 344. In the present embodiment, if the input to the high pass filter 344 becomes saturated, the front end analog signal conditioning circuits 330 provides a '0' output. Alternatively, the first analog-to-digital converter 354 remains unused.

The second analog-to-digital converter 352 accepts the conditioned composite analog signal from the front end signal conditioning circuitry 330 and converts the signal to digital form. In the present embodiment, the second analog to digital converter 356 comprises a single-channel, delta-sigma converter. This converter is advantageous in that it is low cost, and exhibits low noise characteristics. In addition, by using a single-channel converter, there is no need to tune two or more channels to each other. The delta-sigma converter is also advantageous in that it exhibits noise shaping, for improved noise control. An exemplary analog to digital converter is an Analog Devices AD1877JR. In the present embodiment; the second analog to digital converter 356 samples the signal at a 50 Khz sample rate. The output of the second analog to digital converter 356 provides data samples at 50 Khz to the digital signal processing system 334 (FIG. 2).

The digital signal processing system 334 is illustrated in additional detail in FIG. 4. In the present embodiment, the digital signal processing system comprises a microcontroller 360, a digital signal processor 362, a program memory 364, a sample buffer 366, a data memory 368, a read only memory 370 and communication registers 372. In the present embodiment, the digital signal processor 362 is an Analog Devices AD 21020. In the present embodiment, the microcontroller 360 comprises a Motorola 68HC05, with built in program memory. In the present embodiment, the sample buffer 366 is a buffer which accepts the 50 Khz sample data from the analog to digital conversion circuit 332 for storage in the data memory 368. In the present embodiment, the data memory 368 comprises 32 KWords (words being 40 bits in the present embodiment) of dynamic random access memory.

The microcontroller 360 is connected to the DSP 362 via a conventional JTAG Tap line. The microcontroller 360 transmits the boot loader for the DSP 362 to the program memory 364 via the Tap line, and then allows the DSP 362 to boot from the program memory 364. The boot loader in program memory 364 then causes the transfer of the operating instructions for the DSP 362 from the read only memory 370 to the program memory 364. Advantageously, the program memory 364 is a very high speed memory for the DSP 362.

The microcontroller 360 provides the emitter current control and gain control signals via the communications register 372.

Figure 5:
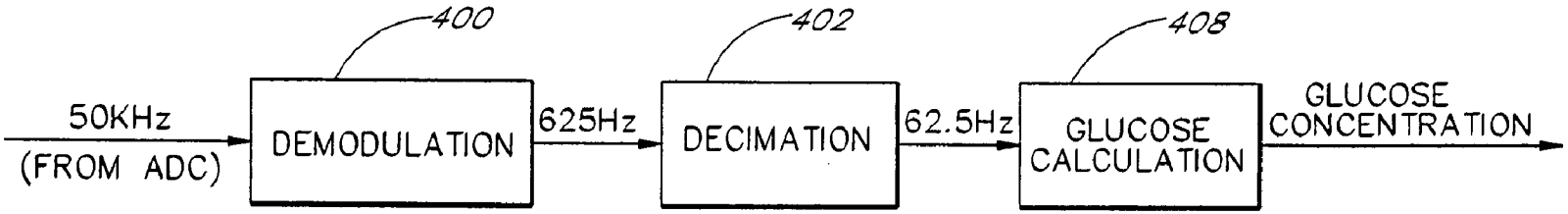
FIG. 5 illustrates additional detail of the operations performed by the digital signal processing circuitry of FIG. 2.

FIGS. 5-8 depict functional block diagrams of the operations of the glucose monitoring system carried out by the digital signal processing system 334. The signal processing functions described below are carried out by the DSP 362 in the present embodiment with the microcontroller 360 providing system management. In the present embodiment, the operation is software/firmware controlled. FIG. 5 depicts a generalized functional block diagram for the operations performed on the 50 Khz sample data entering the digital signal processing system 334. As illustrated in FIG. 5, a demodulation, as represented in a demodulation module 400, is first performed. Decimation, as represented in a decimation module 402 is then performed on the resulting data. Then, the glucose concentration is determined, as represented in a Glucose Calculation module 408.

In general, the demodulation operation separates each emitter signal from the composite signal and removes the 625 Hz carrier frequency, leaving raw data points. The raw data points are provided at 625 Hz intervals to the decimation operation which reduces the samples by an order of 10 to samples at 62.5 Hz. The decimation operation also provides some filtering on the samples. The resulting data is subjected to normalization (which essentially generates a normalized AC/DC signal) and then glucose concentration is determined in the Glucose Calculation module 408.

Figure 6:
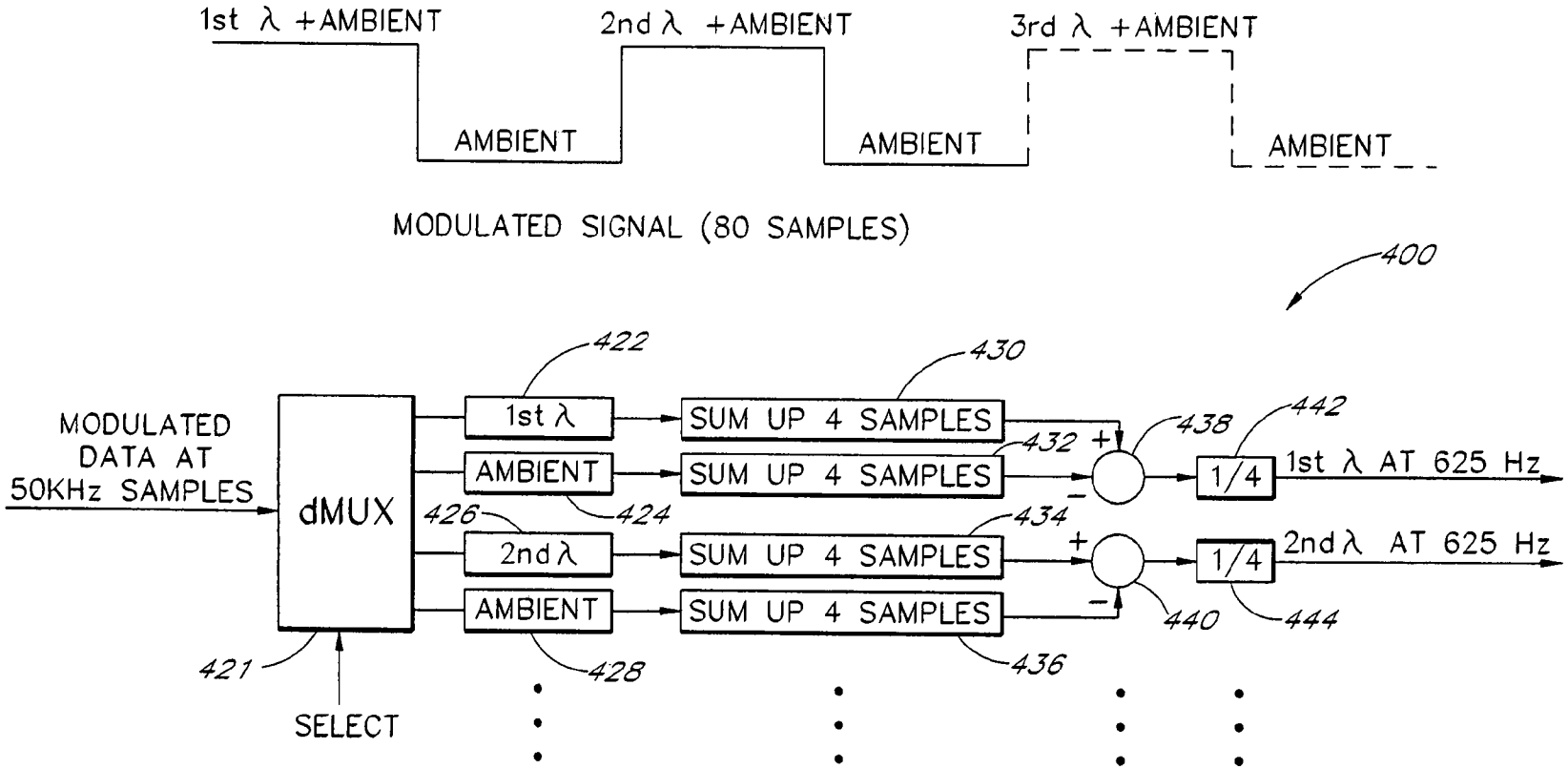
FIG. 6 illustrates additional detail regarding the demodulation module of FIG. 5.

FIG. 6 illustrates the operation of the demodulation module 400. The modulated signal format is depicted in FIG. 6. The pulses for the first three wavelengths of one full 625 Hz cycle of the composite signal is depicted in FIG. 6 with the first tenth cycle being the active first emitter light plus ambient light signal, the second tenth cycle being an ambient light signal, the third tenth cycle being the active second emitter light plus ambient light signal, and the fourth tenth cycle being an ambient light signal, and so forth for each emitter. The sampling frequency is selected at 50 Khz so that the single full cycle at 625 Hz described above comprises 80 samples of data, eight samples relating to the first emitter wavelength plus ambient light, eight samples relating to ambient light, eight samples relating to the second emitter wavelength plus ambient light, eight more samples related to ambient light and so forth until there are eight samples of each emitter wavelength followed by eight samples of ambient light.

Because the signal processing system 334 controls the activation of the light emitters 301-305, the entire system is synchronous. The data is synchronously divided (and thereby demodulated) into the eight-sample packets, with a time division demultiplexing operation as represented in a demultiplexing module 421. One eight-sample packet 422 represents the first emitter wavelength plus ambient light signal; a second eight-sample packet 424 represents an ambient light signal; a third eight-sample packet 426 represents the attenuated second emitter wavelength light plus ambient light signal; and a fourth eight-sample packet 428 represents the ambient light signal. Again, this continues until there is a eight-sample packet for each emitter active period with an accompanying eight-sample packet for the corresponding ambient light period. A select signal synchronously controls the demultiplexing operation so as to divide the time-division multiplexed composite signal at the input of the demultiplexer 421 into its representative subparts or packets.

A sum of the four last samples from each packet is then calculated, as represented in the summing operations 430, 432, 434, 436 of FIG. 6. It should be noted that similar operations are performed on the remaining wavelengths. In other words, at the output of the demodulation operation, five channels are provided in the present embodiment. However, only two channels for two wavelengths are depicted in FIG. 6 for simplicity in illustration. The last four samples are used from each packet because a low pass filter in the analog to digital converter 356 of the present embodiment has a settling time. Thus, collecting the last four samples from each eight-sample packet allows the previous signal to clear. The summing operations 430, 432, 434, 436 provide integration which enhances noise immunity. The sum of the respective ambient light samples is then subtracted from the sum of the emitter samples, as represented in the subtraction modules 438, 440. The subtraction operation provides some attenuation of the ambient light signal present in the data. In the present embodiment, it has been found that approximately 20 dB attenuation of the ambient light is provided by the operations of the subtraction modules 438, 440. The resultant emitter wavelength sum values are divided by four, as represented in the divide by four modules 442, 444. Each resultant value provides one sample each of the emitter wavelength signals at 625 Hz.

It should be understood that the 625 Hz carrier frequency has been removed by the demodulation operation 400. The 625 Hz sample data at the output of the demodulation operation 400 is sample data without the carrier frequency. In order to satisfy Nyquist sampling requirements, less than 10 Hz is needed (with an active pulse of about 4 Hz in the present embodiment). Accordingly, the 625 Hz resolution is reduced to 62.5 Hz in the decimation operation.

Figure 7:
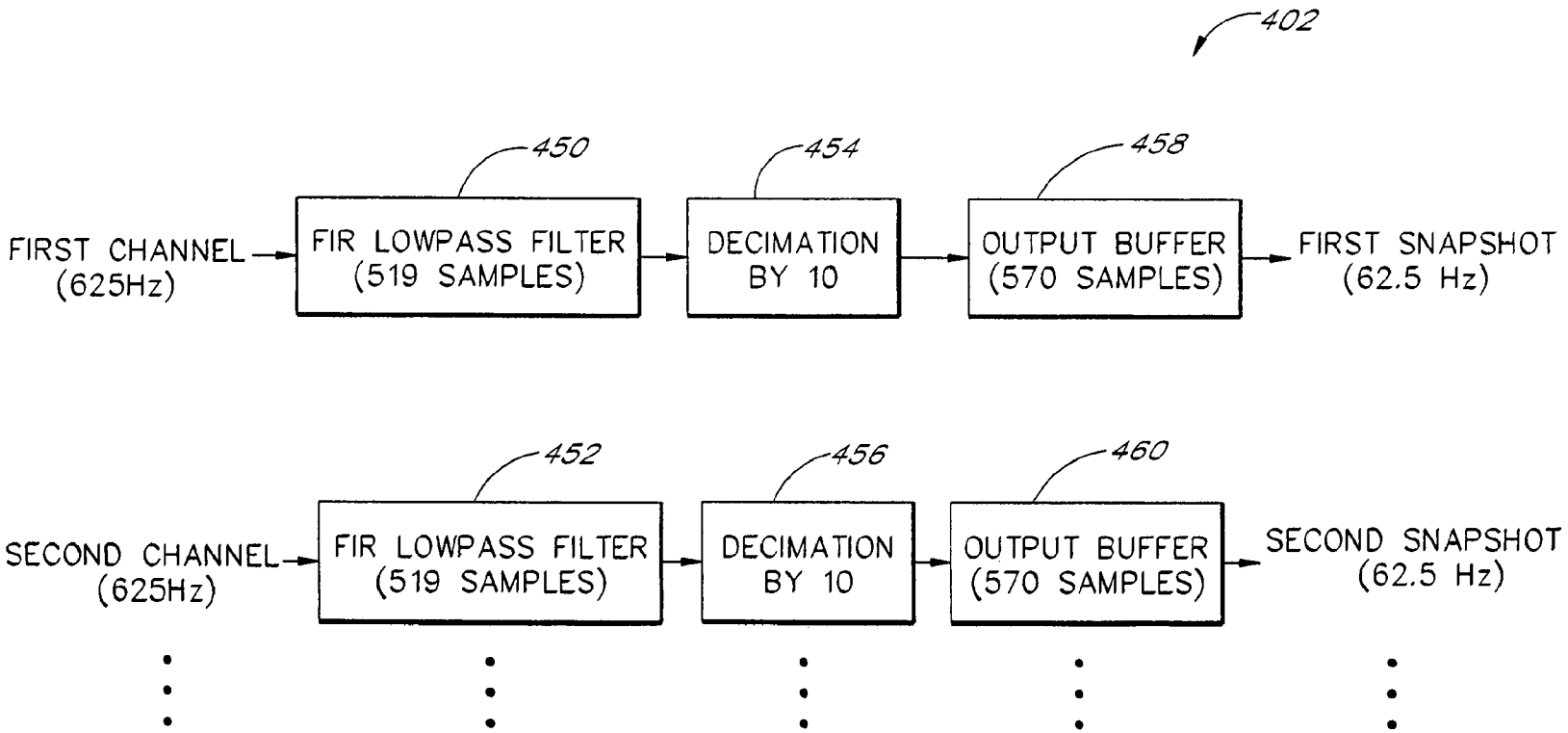
FIG. 7 illustrates additional detail regarding the decimation module of FIG. 5. FIG.

FIG. 7 illustrates the operations of the decimation module 402 for the first two wavelengths. The same operations are also performed on the other wavelength data. Each emitter's sample data is provided at 625 Hz to respective buffer/filters 450, 452. In the present embodiment, the buffer/filters are 519 samples deep. Advantageously, the buffer filters 450, 452 function as continuous first-in, first-out buffers. The 519 samples are subjected to low-pass filtering. Preferably, the low-pass filtering has a cutoff frequency of approximately 7.5 Hz with attenuation of approximately −110 dB. The buffer/filters 450, 452 form a Finite Impulse Response (FIR) filter with coefficients for 519 taps. In order to reduce the sample frequency by ten, the low-pass filter calculation is performed every ten samples, as represented in respective wavelength decimation by 10 modules 454, 456. In other words, with the transfer of each new ten samples into the buffer/filters 450, 452, a new low pass filter calculation is performed by multiplying the impulse response (coefficients) by the 519 filter taps. Each filter calculation provides one output sample for each respective emitter wavelength output buffers 458, 460. In the present embodiment, the output buffers 458, 460 are also continuous FIFO buffers that hold 570 samples of data. The 570 samples provide respective samples or packets (also denoted "snapshot" herein) of samples. As depicted in FIG. 5, the output buffers provide sample data for Glucose Calculation Module 408 for two wavelengths.

Figure 8:
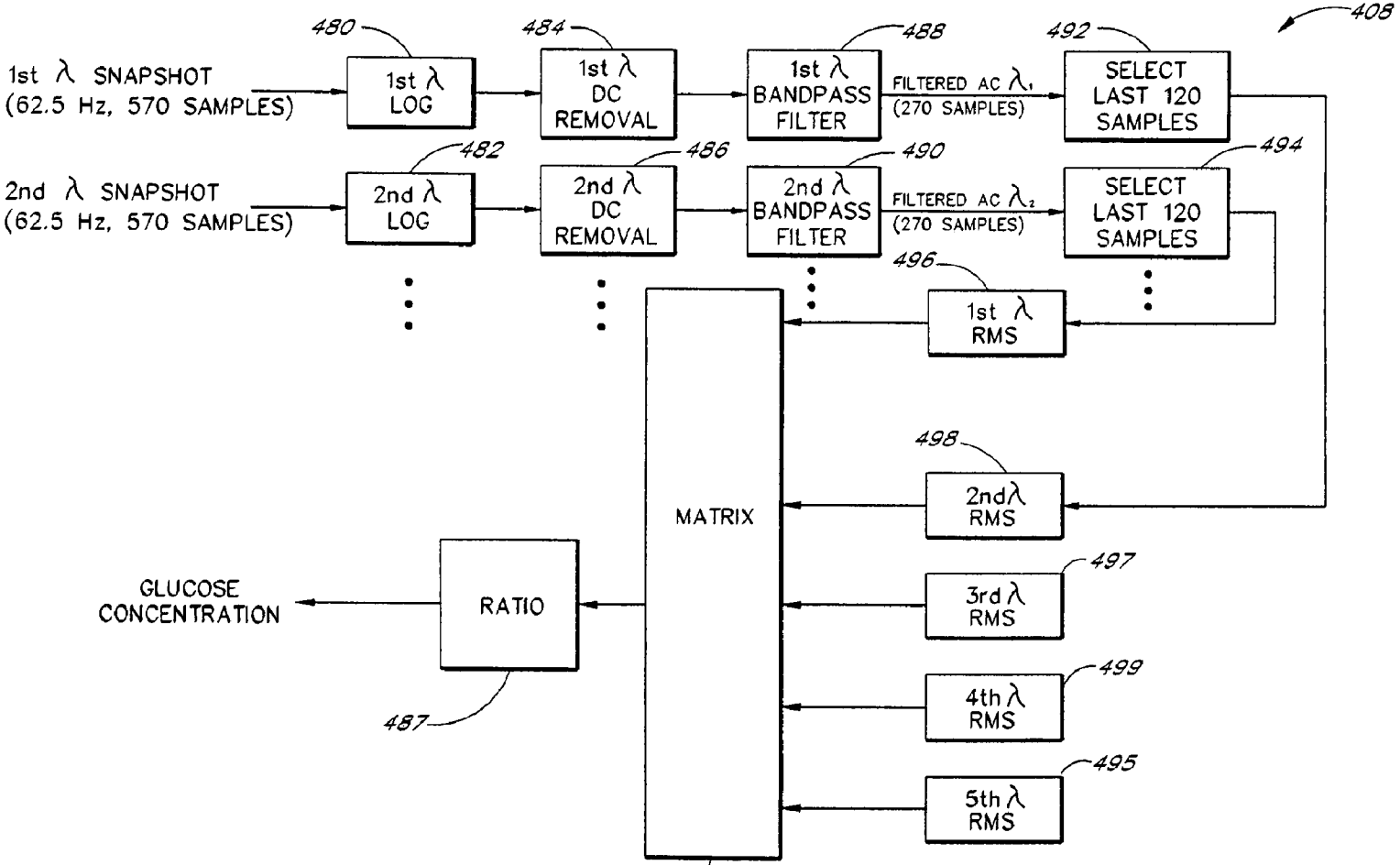
FIG. 8 represents a more detailed block diagram of the operations of the glucose calculation module of FIG. 5.

FIG. 8 illustrates additional functional operation details of the Glucose Calculation module 408. As represented in FIG. 8, the Glucose Calculation operation accepts packets of samples for each wavelength (e.g., 570 samples at 62.5 Hz in the present embodiment) representing the attenuated wavelength signals, with the carrier frequency removed. The respective packets for each wavelength signal are normalized with a log function, as represented in the log modules 480, 482. Again, at this point, only two channels are illustrated in FIG. 8. However, in the present embodiment, five channels are provided, one for each wavelength. The normalization effectively creates an AC/DC normalized signal, this normalization is followed by removal of the DC portion of the signals, as represented in the DC Removal modules 484, 486. In the present embodiment, the DC removal involves ascertaining the DC value of the first one of the samples (or the mean of the first several or the mean of an entire snapshot) from each of the respective wavelength snapshots, and removing this DC value from all samples in the respective packets.

Once the DC signal is removed, the signals are subjected to bandpass filtering, as represented in Bandpass Filter modules 488, 490. In the present embodiment, with 570 samples in each packet, the bandpass filters are configured with 301 taps to provide a FIR filter with a linear phase response and little or no distortion. In the present embodiment, the bandpass filter has a narrow passband from 3.7-4.3 Hz. This provides a narrow passband which eliminates most noise and leaves the portion of the signal due to the active pulse. The 301 taps slide over the 570 samples in order to obtain 270 filtered samples representing the filtered signal of the first emitter wavelength and 270 filtered samples representing the filtered signal of the second emitter wavelength, continuing for each emitter wavelength. In an ideal case, the bandpass filters 488, 490 assist in removing the DC in the signal. However, the DC removal operation 484, 486 also assists in DC removal in the present embodiment.

After filtering, the last 120 samples from each packet (of now 270 samples in the present embodiment) are selected for further processing as represented in Select Last 120 Samples modules 492, 494. The last 120 samples are selected in order to provide settling time for the system.

The RMS for the samples is then determined for each of the 120-sample packets (for each wavelength). The process to obtain the overall RMS values is represented in the RMS modules 495-499.

The resultant RMS values for each wavelength provide normalized intensity values for forming equations according to Beer-Lambert's law. In other words, for Beer-Lambert equation $$I=I_o e^{-(pl*c1*\epsilon 1+pl*c2*\epsilon 2+etc.)} \quad (3)$$

then taking the log of operations 480-482:

$$\ln(I)=\ln(I_o)-(pl*c_1*\epsilon_1+pl*c_2*\epsilon_2+etc.) \quad (4)$$

Then performing DC removal though the DC removal operations 484, 486 and Band pass filter operations 488, 490, the the normalized equation becomes:

$$I_{nom\lambda}=-(pl*c_1*\epsilon_1+pl*c_2*\epsilon_2+etc.) \quad (5)$$

The RMS values (blocks 495-499) for each wavelength provide $I_{norm\lambda}$ for the left side of Equation (7). The extinction coefficients are known for the selected wavelengths.

As will be understood, each equation has a plurality of unknowns. Specifically, each equation will have an unknown term which is the product of concentration and pathlength for each of the constituents of concern (hemoglobin, oxyhemoglobin, glucose and water in the present embodiment). Once a normalized Beer-Lambert equation is formed for each wavelength RMS value (the RMS value representing the normalized intensity for that wavelength), a matrix is formed as follows:

$$I_{nom\lambda 1}=-(\epsilon_{1\lambda 1}c_1+\epsilon_{2\lambda 1}c_2+\epsilon_{3\lambda 1}c_3+\epsilon_{4\lambda 1}c_4+\epsilon_{5\lambda 1}c_5)pl \quad (6)$$

$$I_{nom\lambda 2}=-(\epsilon_{1\lambda 2}c_1+\epsilon_{2\lambda 2}c_2+\epsilon_{3\lambda 2}c_3+\epsilon_{4\lambda 2}c_4+\epsilon_{5\lambda 2}c_5)pl \quad (7)$$

$$I_{nom\lambda 3}=-(\epsilon_{1\lambda 3}c_1+\epsilon_{2\lambda 3}c_2+\epsilon_{3\lambda 3}c_3+\epsilon_{4\lambda 3}c_4+\epsilon_{5\lambda 3}c_5)pl \quad (8)$$

$$I_{nom\lambda 4}=-(\epsilon_{1\lambda 4}c_1+\epsilon_{2\lambda 4}c_2+\epsilon_{3\lambda 4}c_3+\epsilon_{4\lambda 4}c_4+\epsilon_{5\lambda 4}c_5)pl \quad (9)$$

$$I_{nom\lambda 5}=-(\epsilon_{1\lambda 5}c_1+\epsilon_{2\lambda 5}c_2+\epsilon_{3\lambda 5}c_3+\epsilon_{4\lambda 5}c_4+\epsilon_{5\lambda 5}c_5)pl \quad (10)$$

where $C_1$=concentration of water
$C_2$=concentration of hemoglobin
$C_3$=concentration of oxyhemoglobin
$C_4$=concentration of Glucose
$C_5$=concentration of Glucose and $\epsilon_{1\lambda n}$=extinction coefficient for water at $\lambda_n$
$\epsilon_{2\lambda n}$=extinction coefficient for hemoglobin at $\lambda_n$
$\epsilon_{3\lambda n}$=extinction coefficient for oxyhemoglobin at $\lambda_n$
$\epsilon_{4\lambda n}$=extinction coefficient for Glucose at $\lambda_n$
$\epsilon_{5\lambda n}$=extinction coefficient for Glucose at $\lambda_n$ The equations are solved using conventional matrix algebra in order to solve for the product of concentration times pathlength for each constituent, as represented in the Matrix block 489.

In order to remove the path length term, in the present embodiment where glucose is desired, a ratio is performed of the product of pathlength times concentration for glucose to the product of pathlength times the concentration of water as represented in a ratio block 487. Since the pathlength is substantially the same for each wavelength due to normalization (i.e., taking AC/DC) and due to minimal perturbation (e.g., 10%), the pathlength terms cancel, and the ratio indicates the concentration of glucose to water (preferably, this is scaled to mg/dL). The glucose concentration is provided to the display 336.

It should be noted that it may also be possible to create an empirical table by way of experiment which correlates ratios of one or more of the concentration times path length terms to blood glucose concentration.

Figure 2B:
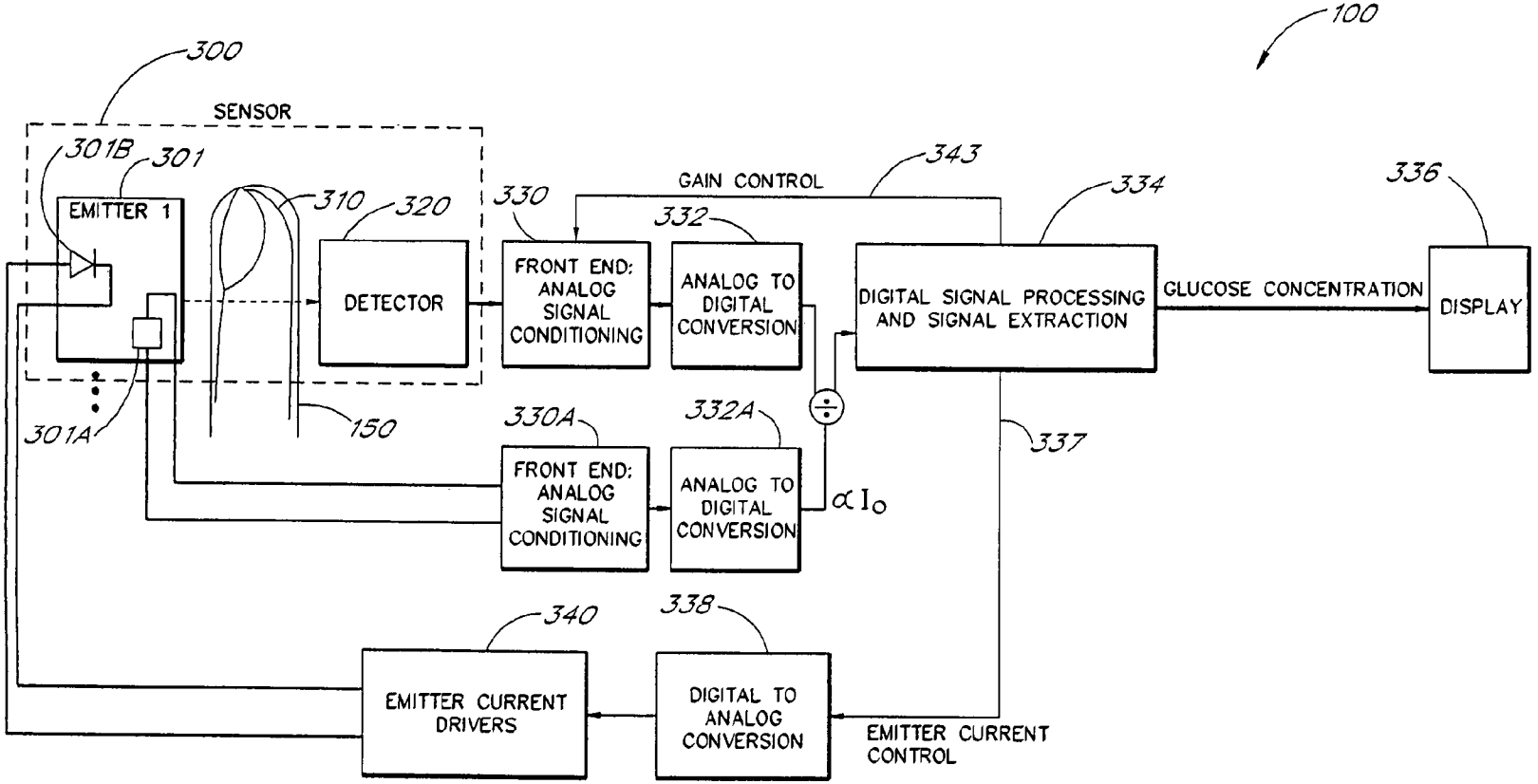
FIG. 2B depicts an embodiment of FIG. 2 with added function for normalizing instabilities in emitters of FIG. 2.
Figure 2C:
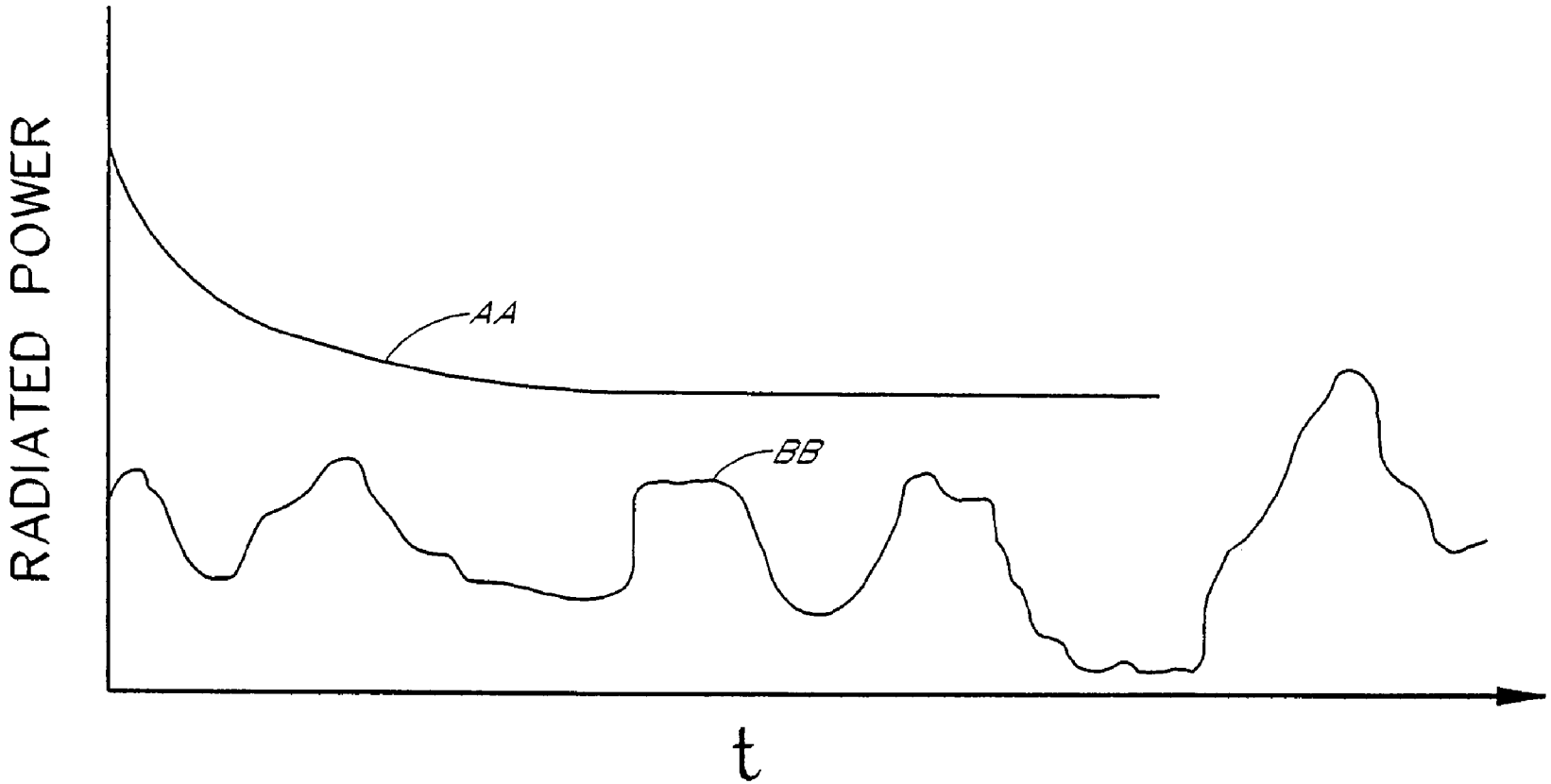
FIG. 2C illustrates a comparison between instabilites in selected emitters.

Even with the emitter driver circuit of FIG. 2A discussed above, infrared LEDs with the longer wavelengths are also inherently unstable with respect to their power transmission. Accordingly, in one advantageous embodiment, the instabilities for the source LEDs can be corrected to accommodate for the instabilities depicted in FIG. 2C. As illustrated in FIG. 2C, two curves are depicted representing transmitted power over time. A first curve labelled AA represents power transmission from LEDs having wavelengths of 660 nm and 905 nm. As illustrated, these emitters have relatively stable power transmission over time. A second curve labelled BB represents power transmission from an emitter with a wavelength of approximately 1330 nm. As illustrated, typical emitters of this wavelength have unstable power transmission over time.

Accordingly, in one embodiment, the emitters in the 1300 nm range are selected as with an integrated photodetector. An appropriate laser diode is an SCW-1300-CD made by Laser Diode, Inc. An appropriate LED is an Apitaxx ETX1300T. With such an emitter, a configuration as depicted in FIG. 2B can be used, whereby the internal photodiode in the emitter is also sampled to detect the initial intensity $l_o$ times a constant ($\alpha$). In general, the signal detected after transmission through the finger is divided by the $\alpha_o$ signal. In this manner, the instability can be normalized because the instability present in the attenuated signal due to instability in the emitter will also be present in the measured $\alpha_o$ signal.

FIG. 2B depicts such an embodiment illustrating only one emitter 301 (of the emitters 301-305). However, all or several of the emitters 301-305 could be emitters having an internal photodiode. As depicted in FIG. 2B, the emitter 301 has an internal photodiode 301a and its LED 301b. As depicted in FIG. 2B, light emitted from the LED 301b in the emitter 301 is detected by a photodiode 301a. The signal from the photodiode 301a is provided to front end analog signal conditioning circuitry 330A. The analog signal conditioning circuitry 330A similar to the analog signal conditioning circuitry 330. However, because the photodiode 301a detects a much stronger intensity compared to the detector 320 (due to attenuation by tissue), different amplification may be required.

After analog signal conditioning in the front end anaolog signal conditioning circuity 330A, the signal from the photodiode 301a is converted to digital form with an analog to digital conversion circuit 332a. Again, it should be understood that the analog to digital conversion circuit 332a can be the same configuration as the analog to digital conversion circuit 332. However, because the signal from the photodiode 301a and the detector 320 appear at the same time, two channels are required.

The attenuated light signal through the finger is detected with the detector 320 and passed through front end analog signal conditioning circuit 330 and is converted-to-digital form in analog to digital conversion circuit 332, as described in further detail below. The signal representing the intensity of the light transmitted through the finger 310 is divided as represented by the division block 333 by the signal which represents the intensity of light from the LED 301b detected by the photodiode 301a.

In this manner, the variations or instability in the initial intensity $l_o$ cancel through the division leaving a corrected intensity which is divided by the constant $\alpha$. When the log is performed as discussed below, and bandpass filtering is performed, the constant .alpha. term is removed leaving a clean signal.

Mathmatically, this can be understood by representing the attenuated signal under Beer-Lambert's Law and the signal from the photodiode 301a as $\alpha l_o$ as discussed above:

Thus, the signal emerging from the analog to digital conversion circuit 332 is as follows:

$$l=l_o e^{\Sigma(-\epsilon * pl * c)}$$

Dividing Equation 3 by $\alpha * l_o$ and simplifying provides the signal after the division operation 333:

$$=(e^{\Sigma(-\epsilon * pl * c)})/\alpha$$

Thus providing a normalized intensity signal for the input to the digital signal processing circuit 334.

Figure 10:
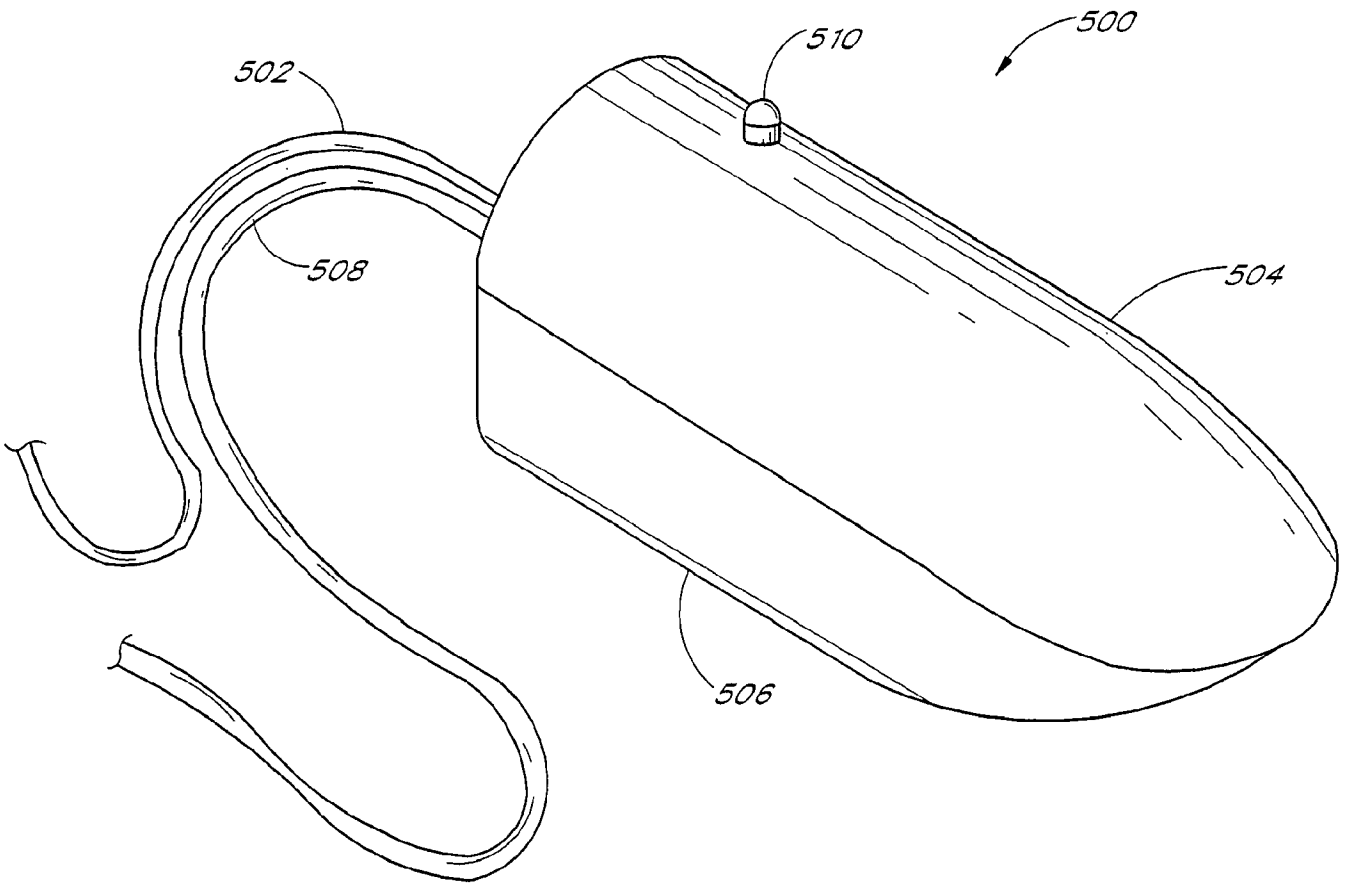
FIGS. 10-12 depict one embodiment of a probe which can be used to induce an active pulse in accordance with the principals of the present invention.

FIG. 10 depicts a perspective view of one alternative embodiment of an inflatable bladder sensor 500 which can be used to induce an active pulse in accordance with the teachings of the present invention. This inflatable bladder sensor 500 is for a bed-side blood glucose monitor. The inflatable bladder sensor 500 has electrical connections 502 for coupling the device to the blood glucose system 299.

Typically, the electrical connection 502 carries sufficient conductors to power the emitters 301-305 and to receive a detector signal from the detector 320.

The inflatable bladder sensor 500 has a curved upper surface 504 and vertical sides 506. The inflatable bladder sensor 500 also has an fluid pressure supply tube 508. In one advantageous embodiment, the supply tube cycles air into and out of an inflatable bladder within the inflatable bladder sensor 500. The fluid supply tube 508 couples to the bedside glucose monitoring system which is equipped with a cycling pump to induce pressure and remove pressure from the supply tube 508. In one embodiment, a pressure relief valve 510 is located on the upper surface 504 to allow release of pressure in the inflatable bladder.

Figure 11:
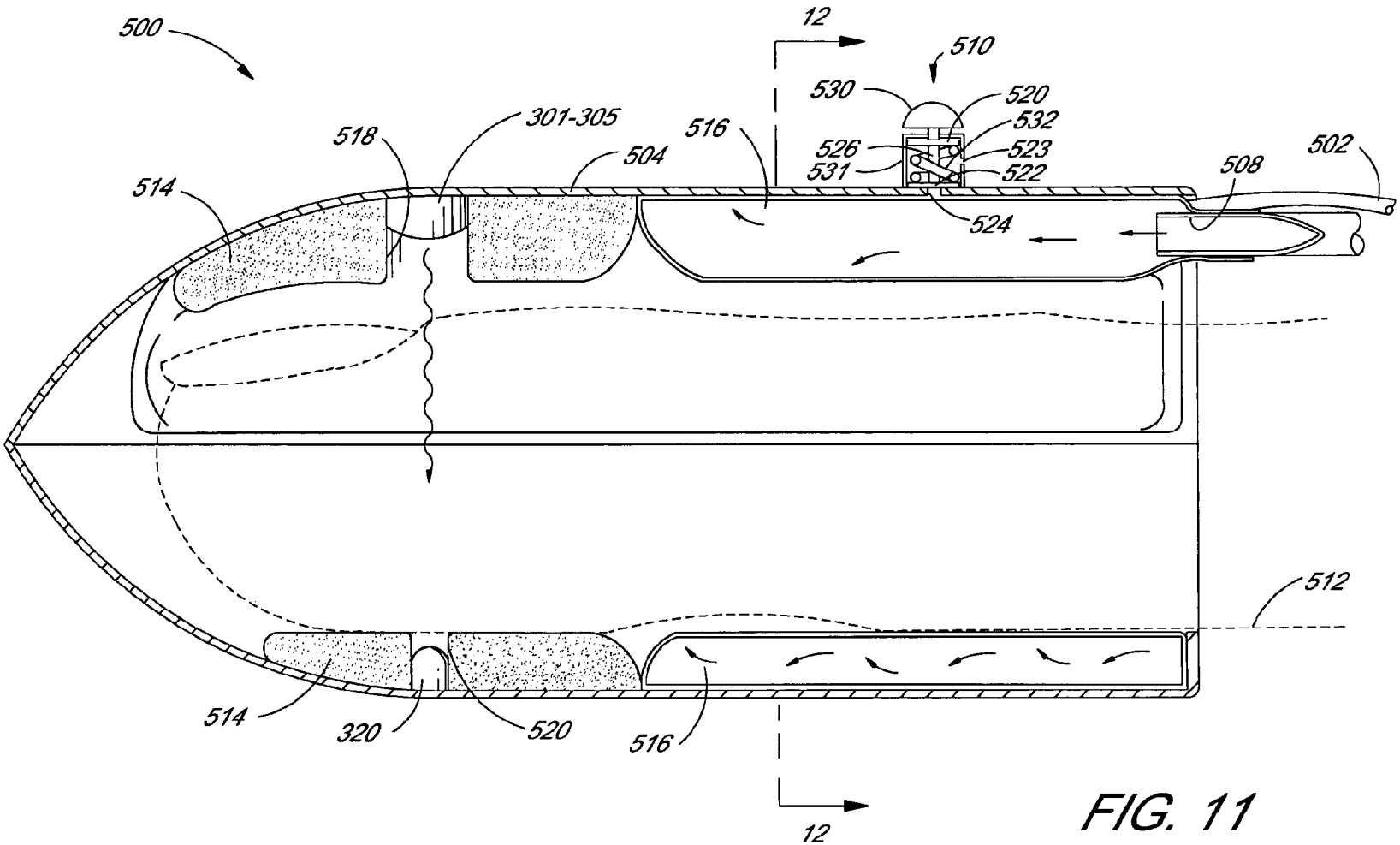

FIG. 11 depicts a cross-sectional view along the inflatable bladder sensor 500 of FIG. 10. As depicted in FIG. 11, a human digit or finger 512 is positioned inside the sensor 500. The finger 512 is positioned is supported by a pad 514 in the area of light transmission. A flexible inflatable bladder 516 surrounds the finger proximally from the area of light transmission. The pad has an an aperture 518 to enable emitters 301-305 to provide unobstructed optical transmission to the surface of finger 512.

Surrounded by the padding 514 and opposite the emitters 301-305 is the detector 320. The detector 320 is positioned within an aperture 520 in the pad 514 to ensure that photodetector is separated from the finger 512. A serpentine arrow is shown extending from the light emitters 301-305 to the detector 320 to illustrate the direction of propagation of light energy through the finger 512.

Relief valve 510 enables manual and automatic release of pressure in the inflatable bladder 516. Relief valve 510 has a valve plate 522 which is spring biased to seal an aperture 524 using spring 532. The valve plate is connected to relief valve shaft 526. A valve button 530 is coupled to the valve shaft. The valve shaft extends through a valve housing 531 which forms a cylindrical sleeve shape. The valve housing is coupled to the upper surface 504 of sensor 500. The valve housing has an aperture 523 which allows air to readily escape from the relief valve. Preferably, the relief valve is designed to ensure that the pressure is not high enough to cause damage to nerves. Accordingly, if the pressure increases beyond a certain point, the relief valve allows the excess fluid to escape, thereby reducing the pressure to the maximum allowable limit. Such pressure relief valves are well understood in the art. Relief valve 510 could also be a spring-loaded needle-type valve.

Figure 12A:
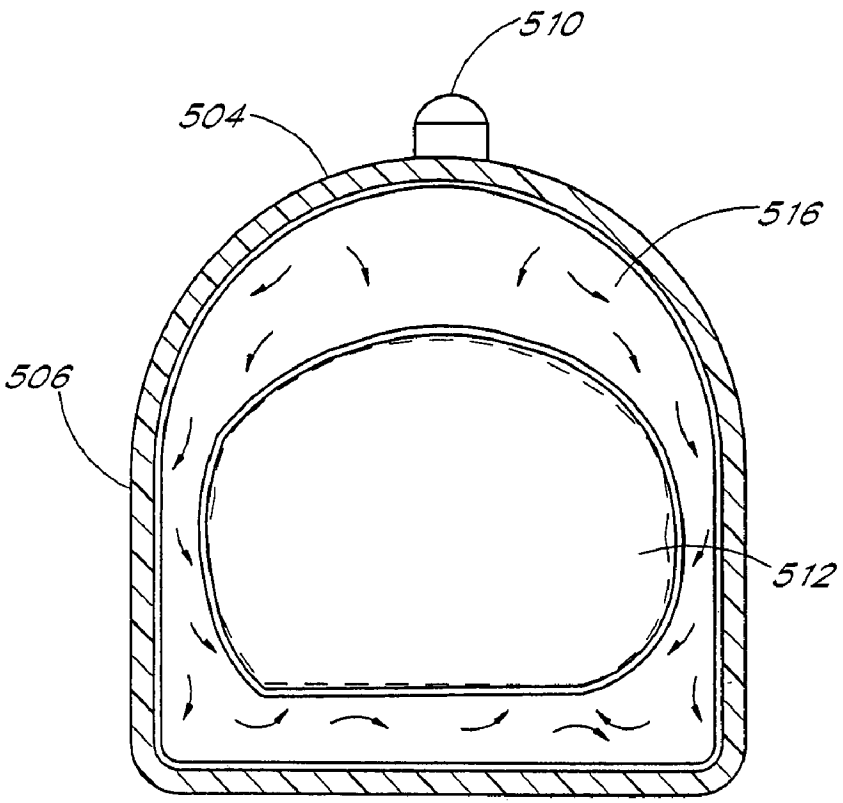
Figure 12:
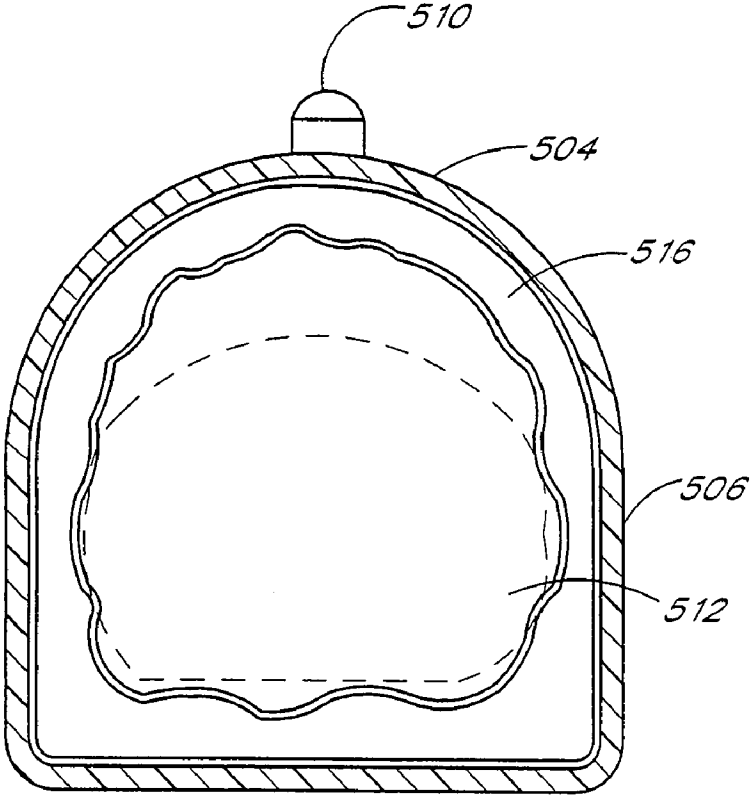

FIG. 12 depicts a sectional view along line 12-12 of FIG. 11 to illustrate the state of the sensor 500 when the inflatable bladder 516 is deflated. FIG. 12a depicts the same sectional view as FIG. 12 with the bladder 516 inflated.

With this configuration, the blood glucose system can cycle fluid into and out of the inflatable bladder 516 at the selected rate to actively induce a pulse of sufficient magnitude as discussed above.

Additional Application of Active Pulse

As discussed in the co-pending U.S. patent application Ser. No. 08/320,154 filed Oct. 7, 1994, now U.S. Pat. No. 5,632,272 which is incorporated herein by reference, a saturation transform may be applied to each 120 sample packet. It has been found that a second maxima representing venous oxygen saturation exists in the Master Power Curve during motion of the patient. In view of this, it is possible to utilize the inducement of a pulse disclosed herein through physically perturbing the medium under test in order to obtain the second maxima in the Master Power Curve, and thereby obtain the venous oxygen saturation if desired. The modulation may be lower than 10% because hemoglobin and oxyhemoglobin concentrations are higher than glucose and absorbtion at 660 nm and 905 nm are relatively strong. Thus, modulation from 1-5% may provide adequate results.

Although the preferred embodiment of the present invention has been described and illustrated above, those skilled in the art will appreciate that various changes and modifications to the present invention do not depart from the spirit of the invention. For example, the principles and method of the present invention could be used to detect trace elements within the bloodstream (e.g., for drug testing, etc.). Accordingly, the scope of the present invention is limited only by the scope of the following appended claims.

What is claimed is:

[1. A system for non-invasively monitoring concentrations of blood constituents in a living subject, said system comprising:

a light source configured to be positioned at a measurement site and further configured to irradiate a fleshy medium of a living subject with radiation at a plurality of wavelengths selected for attenuation sensitivity to at least one of a plurality of blood constituent concentrations, said plurality of blood constituent concentrations including a glucose concentration;

an optical detector configured to be positioned at said measurement site to detect only light which has been attenuated by said fleshy medium at said measurement site, said optical detector configured to generate an output signal indicative of an intensity of said radiation after attenuation through said fleshy medium;

a signal processor responsive to said output signal to analyze said output signal to extract portions of said signal due to optical characteristics of said blood to determine a concentration of at least one selected constituent within said subject's bloodstream; and a pressure application device configured to be positioned at a location different from said measurement site to avoid applying direct pressure to said measurement site while causing a change in a volume of blood in the fleshy medium at said measurement site sufficient to alter said output signal to increase a likelihood that said signal processor can determine at least said glucose concentration.]

[2. The system of claim 1, wherein said change in said volume of blood alters said output signal such that a difference in said output signal at a full blood volume and said output signal at said changed output volume comprises about 1 to about 10 percent.]

[3. The system of claim 2, wherein said difference comprises about 10 percent.]

[4. The system of claim 1, wherein at least one of said plurality of wavelengths comprises about 660 nanometers (nm).]

[5. The system of claim 4, wherein said at least one wavelength is selected for attenuation sensitivity to a hemoglobin concentration.]

[6. The method of claim 1, wherein said light source comprises two or more light emitting diodes.]

[7. A method of non-invasively monitoring concentrations of blood constituents in a living subject, said method comprising:

irradiating a fleshy medium of a living subject at a measurement site with radiation at a plurality of wavelengths selected for attenuation sensitivity to at least one of a plurality of blood constituent concentrations, said plurality, of blood constituent concentrations including a glucose concentration;

detecting at said measurement site only light which has been attenuated by said fleshy medium;

outputting a signal indicative of the intensity of said radiation after attenuation through said fleshy medium;

extracting portions of said signal due to optical characteristics of said blood to determine a concentration of at least one selected constituent within said subject's bloodstream;

using a device external to said fleshy medium, changing a volume of blood in the fleshy medium at said measurement site sufficient to alter said output signal to increase a likelihood that at least said glucose concentration can be determined without applying direct mechanical pressure to said fleshy medium at said measurement site; and causing said glucose concentration to be displayed.]

[8. A method of non-invasively monitoring glucose concentrations in a living subject, said method comprising:

applying pressure at a first location to a fleshy medium to increase a likelihood of determining a glucose concentration in a living subject;

detecting only light attenuated by said fleshy medium at a second location different from said first location, wherein said applying pressure does not apply direct mechanical pressure to said second location;

outputting a signal indicative of said detected attenuated light, wherein said signal includes information about said glucose concentration at a resolution differentiable from noise or other blood constituents;

determining at least said glucose concentration; and causing said glucose concentration to be displayed.]

[9. A system for non-invasively monitoring concentrations of blood constituents in a living subject, said system comprising:

a light source configured to be positioned at a measurement site and further configured to irradiate a fleshy medium of a living subject with radiation at a plurality of wavelengths selected for attenuation sensitivity to at least one of a plurality of blood constituent concentrations, said plurality of blood constituent concentrations including a glucose concentration, wherein said light source comprises two or more light emitting diodes;

an optical detector configured to be positioned at said measurement site to detect light which has been attenuated by said fleshy medium, said optical detector configured to generate an output signal indicative of the intensity of said radiation after attenuation through said fleshy medium;

a signal processor responsive to said output signal to analyze said output signal to extract portions of said signal due to optical characteristics of said blood to determine a concentration of at least one selected constituent within said subject's bloodstream; and a pressure application device configured to be positioned at a location different from said measurement site to avoid applying direct pressure to said measurement site while causing a change in a volume of blood in the fleshy medium at said measurement site sufficient to alter said output signal to increase a likelihood that said signal processor can determine at least said glucose concentration.]

[10. The system of claim 9, wherein said optical detector detects light which has been attenuated by said fleshy medium at one location.]

[11. The system of claim 9, wherein the pressure application device comprises an inflatable bladder.]

[12. The system of claim 9, further comprising a temperature variation element.]

[13. The system of claim 12, wherein said temperature variation element cyclically varies the temperature of said fleshy medium in order to induce a change in the flow of blood in said fleshy medium.]

[14. The system of claim 9, wherein said two or more light emitting diodes are configured to produce light at a plurality of wavelengths, each wavelength selected for attenuation sensitivity to determine a concentration of said at least one selected constituent.]

[15. A method of non-invasively monitoring concentrations of blood constituents in a living subject, said method comprising:

irradiating a fleshy medium of a living subject at a measurement site with radiation at a plurality of wavelengths selected for attenuation sensitivity to at least one of a plurality of blood constituent concentrations, said plurality of blood constituent concentrations including a glucose concentration, wherein irradiating comprises using two or more light emitting diodes;

detecting at said measurement site light which has been attenuated by said fleshy medium;

outputting a signal indicative of the detected light;

extracting portions of said signal due to optical characteristics of said blood to determine a concentration of at least one selected constituent within said subject's bloodstream;

using a device external to said fleshy medium, changing a volume of blood in the fleshy medium at said measurement site sufficient to alter said output signal to increase a likelihood that at least said glucose concentration can be determined without applying direct mechanical pressure to said fleshy medium at said measurement site; and causing said glucose concentration to be displayed.]

[16. The method of claim 15, wherein the step of detecting further comprise detecting at said measurement site light which has been attenuated by said fleshy medium at one location.]

[17. A method of non-invasively monitoring glucose concentrations in a living subject, said method comprising:

irradiating a fleshy medium of a living subject using two or more light emitting diodes;

applying pressure at a first location to a fleshy medium to increase a likelihood of determining a glucose concentration in a living subject;

detecting light attenuated by said fleshy medium at a second location different from said first location, wherein said applying pressure does not apply direct mechanical pressure to said fleshy medium at said second location;

outputting a signal indicative of said detected attenuated light, wherein said signal includes information about said glucose concentration at a resolution differentiable from noise or other blood constituents;

determining at least said glucose concentration; and causing glucose concentration to be displayed.]

[18. The method of claim 17, wherein the step of detecting further comprises detecting light attenuated through a single location of said fleshy medium.]

[19. The method of claim 17, wherein applying pressure comprises inflating a bladder.]

[20. The method of claim 17, further comprising cyclically varying the temperature of said fleshy medium in order to induce a change in the flow of blood in said fleshy medium.]

*21. A system for non-invasively monitoring a blood constituent in a living subject, said system comprising:*

*a light source configured to be positioned at a measurement site and further configured to irradiate a fleshy medium of a living subject with radiation at a plurality of wavelengths selected for attenuation sensitivity to at least one of a plurality of blood constituents;*

*an optical detector configured to be positioned at said measurement site to detect light which has been attenuated by said fleshy medium at said measurement site, said optical detector configured to generate an output signal indicative of an intensity of said radiation after attenuation through said fleshy medium;*

*a signal processor responsive to said output signal to analyze said output signal to extract portions of said signal due to optical characteristics of said blood to determine a level of at least one selected constituent within said subject's bloodstream; and*

*a pressure application device configured to be positioned at a location different from said measurement site to avoid applying direct pressure to said measurement site while causing a change in a volume of blood in the fleshy medium at said measurement site sufficient to alter said output signal to increase a likelihood that said signal processor can determine said level, wherein said change in said volume of blood comprises causing evacuation of a volume of blood at said measurement site.*

*22. The system of claim 21, wherein said at least one selected constituent within said subject's bloodstream comprises glucose.*

*23. The system of claim 21, wherein said at least one selected constituent within said subject's bloodstream comprises hemoglobin.*

*24. The system of claim 21, wherein said at least one selected constituent within said subject's bloodstream comprises oxyhemoglobin.*

*25. The system of claim 21, wherein said at least one selected constituent within said subject's bloodstream comprises carboxyhemoglobin.*

*26. The system of claim 21, wherein a measure of said at least one selected constituent within said subject's bloodstream comprises oxygen saturation.*

*27. The system of claim 21, wherein a measure of said at least one selected constituent within said subject's bloodstream comprises venous oxygen saturation.*

*28. The system of claim 21, wherein said at least one selected constituent within said subject's bloodstream comprises protein.*

*29. The system of claim 21, wherein said at least one selected constituent within said subject's bloodstream comprises fat.*

*30. The system of claim 21, wherein said at least one selected constituent within said subject's bloodstream comprises cholesterol.*

*31. The system of claim 21, wherein said at least one selected constituent within said subject's bloodstream comprises a therapeutic drug.*

*32. The system of claim 21, wherein said at least one selected constituent within said subject's bloodstream comprises a drug of abuse.*

* * * * *

UNITED STATES PATENT AND TRADEMARK OFFICE

CERTIFICATE OF CORRECTION

PATENT NO. : RE42,753 E
APPLICATION NO. : 12/497517
DATED : September 27, 2011
INVENTOR(S) : Esmaiel Kiani-Azarbayjany et al.

It is certified that error appears in the above-identified patent and that said Letters Patent is hereby corrected as shown below:

IN THE DRAWINGS:

On Sheet 12 of 16 (Opposite Referral Numeral 166) (FIG. 9), Line 1, change "[log(log9average" to --[log(log(average--.

In Column 16, Line 9, change "ln(I)" to --ln(l)--.

In Column 16, Line 14, change "$l_{non\lambda}$" to --$l_{norm\lambda}$--.

In Column 16, Line 28, change "$l_{non\lambda 1}$" to --$l_{norm\lambda 1}$--.

In Column 16, Line 30, change "$l_{non\lambda 2}$" to --$l_{norm\lambda 2}$--.

In Column 16, Line 32, change "$l_{non\lambda 3}$" to --$l_{norm\lambda 3}$--.

In Column 16, Line 34, change "$l_{non\lambda 4}$" to --$l_{norm\lambda 4}$--.

In Column 16, Line 36, change "$l_{non\lambda 5}$" to --$l_{norm\lambda 5}$--.

Signed and Sealed this
Nineteenth Day of June, 2012

David J. Kappos

David J. Kappos
*Director of the United States Patent and Trademark Office*